United States Patent
Sauzeau et al.

(10) Patent No.: US 11,607,419 B2
(45) Date of Patent: Mar. 21, 2023

(54) INHIBITORS OF RAC1 AND USES THEREOF FOR INDUCING BRONCHODILATATION

(71) Applicants: INSTITUT NATIONAL DE LA SANTE ET DE LA RECHERCHE MEDICALE (INSERM), Paris (FR); CENTRE NATIONAL DE LA RECHERCHE SCIENTIFIQUE, Paris (FR); UNIVERSITE DE NANTES, Nantes (FR); CHU NANTES, Nantes (FR)

(72) Inventors: Vincent Sauzeau, Bouguenais (FR); Gervaise Loirand, Thouare-sur-Loire (FR); Jacques Lebreton, Nantes (FR); Arnaud Tessier, Orvault (FR); Agnes Quemenier, Nantes (FR)

(73) Assignees: INSERM (INSTITUT NATIONAL DE LA SANTE ET DE LA RECHERCHE MEDICALE), Paris (FR); CENTRE NATIONAL DE LA RECHERCHE SCIENTIFIQUE, Paris (FR); UNIVERSITE DE NANTES, Nantes (FR); CHU NANTES, Nantes (FR)

(*) Notice: Subject to any disclaimer, the term of this patent is extended or adjusted under 35 U.S.C. 154(b) by 8 days.

(21) Appl. No.: 16/620,237

(22) PCT Filed: Jun. 6, 2018

(86) PCT No.: PCT/EP2018/064920
§ 371 (c)(1),
(2) Date: Dec. 6, 2019

(87) PCT Pub. No.: WO2018/224560
PCT Pub. Date: Dec. 13, 2018

(65) Prior Publication Data
US 2021/0077508 A1    Mar. 18, 2021

(30) Foreign Application Priority Data
Jun. 6, 2017 (EP) ..................... 17305662

(51) Int. Cl.
*A61K 31/63* (2006.01)
*A61P 11/06* (2006.01)

(52) U.S. Cl.
CPC .............. *A61K 31/63* (2013.01); *A61P 11/06* (2018.01)

(58) Field of Classification Search
CPC ................................ A61K 31/63; A61P 11/06
See application file for complete search history.

(56) References Cited

U.S. PATENT DOCUMENTS

| 2,192,490 A | 3/1940 | Warnat |
| 2,407,309 A | 9/1946 | Lott et al. |
| 5,932,599 A | 8/1999 | Boes et al. |
| 6,521,658 B1 | 2/2003 | Li et al. |
| 2013/0165523 A1 | 6/2013 | Blangy |

(Continued)

FOREIGN PATENT DOCUMENTS

| CN | 101 429 142 A | 5/2009 |
| EP | 1344525 A1 | 9/2003 |
| JP | 1998067734 | 3/1998 |

(Continued)

OTHER PUBLICATIONS

Doddareddy et al: "Hologram quantitative structure activity relationship studies on 5-HT6 antagonists", Bioorganic & Medical Chemistry, vol. 12, No. 14, pp. 3815-3824, Jul. 1, 2004.

Kompis et al: "DNA and RNA Synthesis: Antifolates", Chemical Reviews, vol. 105, No. 2, pp. 593-620, Feb. 1, 2005.

Zheng et al: "Analgesic agents without gastric damage: Design and synthesis structurally simple benzenesulfonanilide-type cyclooxygenase-1-selective inhibitors", vol. 15, No. 2, pp. 1014-1021, Dec. 12, 2006.

Zheng et al: "Corrigendum to "Analgesic agents withour gastric damage: Design and synthesis of structurally simple benzenesulfonanilide-type cyclooxygenase-1-selective inhibitors" [Bioorg. Med. Chem. 15 (2007) 1014-1021]", Bioorganic & Medical Chemistry, vol. 15, No. 9, pp. 3299-3300, Mar. 29, 2007.

(Continued)

*Primary Examiner* — Marcos L Sznaidman
(74) *Attorney, Agent, or Firm* — WCF IP

(57) ABSTRACT

The present invention concerns a compound having the following formula (I): wherein: —A is in particular —N(R'$_a$)—C(=O)—R, R'$_a$ being H or a ($C_1$-$C_6$)alkyl group, and R being preferably a group having the following formula (II): —X is in particular chosen from the group consisting of: —$SO_2$—N(R'$_b$)—, R'$_b$ being H or a ($C_1$-$C_6$) alkyl group, —N(R''$_b$)—$SO_2$—, R''b being H or a ($C_1$-$C_6$) alkyl group, —CO—NH—, and —NH—CO—, for use for the treatment of pathologies characterized by bronchoconstriction, such as asthma.

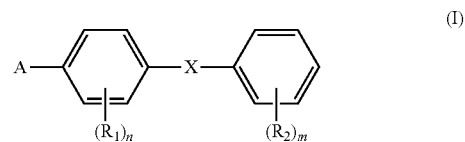

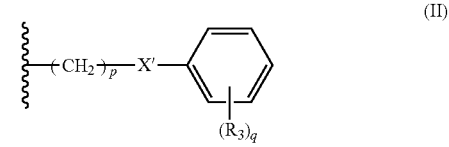

6 Claims, 6 Drawing Sheets

(56) References Cited

U.S. PATENT DOCUMENTS

Figure 1:
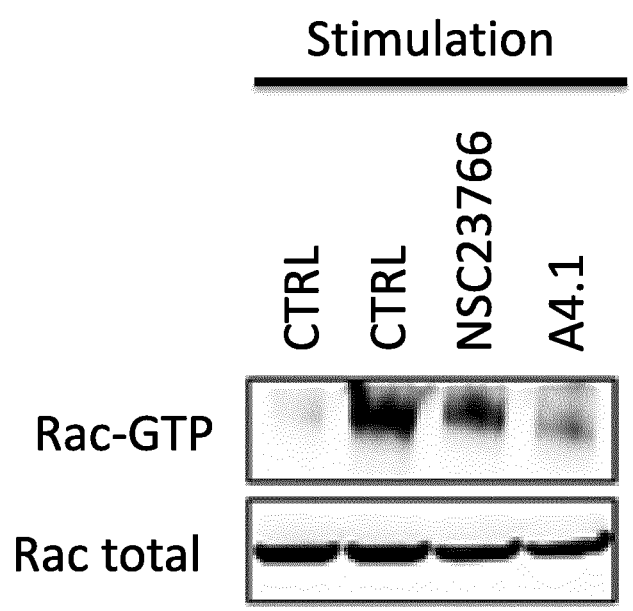

2013/0273034 A1* 10/2013 Bair .................. C07D 213/74
424/133.1
2014/0378507 A1* 12/2014 Kang .................. A61K 31/47
514/603

FOREIGN PATENT DOCUMENTS

| JP | 2002243473 | A | 2/2002 |
|----|------------|---|--------|
| JP | 2020524136 | A | 8/2020 |
| WO | 2001/098274 | A2 | 12/2001 |
| WO | 200303082881 | A2 | 10/2003 |
| WO | 2005/013914 | A2 | 2/2005 |
| WO | 2007/003934 | A2 | 1/2007 |
| WO | 2012/142698 | A1 | 10/2012 |
| WO | 2013/009799 | A1 | 1/2013 |
| WO | 2018224563 | A1 | 12/2018 |

OTHER PUBLICATIONS

Database Caplus [online], Shenghui et al: "Nitrogen containing polyhydroxylated aromatics as HIV-1 integrase inhibitors", Chemical Abstracts Service, Columbus, Ohio, US, Jan. 1, 2012.
Perlovich et al: "Thermodynamic aspects of solubility and partitioning processes of some sulfonamides in the solvents modeling biological media", Journal of Chemical Thermodynamics, vol. 69, pp. 56-65, Oct. 3, 2013.
Lawrence et al: "Synthesis and biological evaluation of naphthoquinone analogs as a novel class of proteasome inhibitors", vol. 18, No. 15, pp. 5576-5592, Aug. 1, 2010.
Masevicius et al: "4-Amino-5-(arylaminomethyl)-2-(methylthio)furo[2,3-d]pyrimidines via Mitsunobu Reaction of 4-Amino-5(hydroxymethyl)-2-(methylthio)furo[2,3-d]pyrimidine with N-Mesyl- and N-Nosylarylamines", Synthesis, vol. 44, No. 9, pp. 1329-1338, Mar. 27, 2012.
Database Registy [online], "N-(3,4-Dimethoxyphenyl)-4-Nitrobenzenesul Fonamide", Chemical Abstracts Service, Columbus, Ohio, US, Jul. 15, 2004.
Database Registry [online], "4-Amino-N-(2,4-Dimetheoxyphenyl)Benzenesulfonamide", Chemical Abstracts Service, Columbus, Ohio, US, Nov. 11, 2007.
Database Registry [online], "N-(3,5-Dimethoxyphenyl)-4-Nitro-Benzenesulfonamide", Chemical Abstracts Service, Columbus, Ohio, US, Jun. 3, 2012.
Database Registry [online], "4-Amino-N-(3-Methylthio-Phenyl)-Benzenesulfonamide", Chemical Abstracts Service, Columbus, Ohio, US, Apr. 23, 2008.
Database Registy [online], "4-Amino-N-(2,5-Dimethoxyphenyl)Benzenesulphonamide", Chemical Abstracts Service, Columbus, Ohio, US, Sep. 24, 1998.
Anonymous: Amino acid registry, 2016.
Gaind et al: "Sulfonamides, II", Journal of the Indian Chemical Society, vol. 18, p. 209-212, 1941.
Yu, S. et al., "Nitrogen-containing polyhydroxylated aromatics as HIV-1 integrase inhibitors: synthesis, structure-activity relationship analysis, and biological activity", Journal of Enzyme Inhibition and Medicinal Chemistry 27 No. 5, 2012.
Le Pera, A. et al., "Highly specific N-monomethylation of primary aromatic amines", Tetrahedron 62, 2006.
Database Registry [online], 528580-84-9: Acetamide, Jun. 10, 2003.
Database Registry [online], 642998-77-4: Propanamide, Jan. 29, 2004.
Database Registry [online], 663165-55-7: Acetamide, Mar. 15, 2004.
Database Registry [online], 331240-24-5: Benzenesulfonamide, Apr. 13, 2001.
Database Registry [online], 694515-65-6: Propanamide, Jun. 17, 2004.
Database Registry [online], 943082-65-3: Carbamic Acid, Jul. 22, 2007.

* cited by examiner

INHIBITORS OF RAC1 AND USES THEREOF FOR INDUCING BRONCHODILATATION

The present invention concerns new inhibitors of RAC1, as well as pharmaceutical compositions comprising said inhibitors. The present invention also concerns said compounds for use for treating asthma.

Asthma is a heterogeneous inflammatory disorder of the airways characterized by chronic deregulated inflammation, bronchial hyperreactivity, and by symptoms of recurrent wheezing, coughing, and shortness of breath. Its prevalence has increased considerably over the past three decades, particularly in Western countries. Asthma is a major public health problem that affects 300 million people worldwide. Classically, the airway smooth muscle cells contribute to the pathogenesis of asthma mainly through its contractile properties: airway hyperresponsiveness (AHR), one of the main characteristics in asthma, refers to excessive contractile response of airway smooth muscle cells. The degree of AHR correlates with asthma severity and the need for therapy.

Regular treatment is composed by the inhalation of corticosteroids and long-acting beta2-adrenergic receptor agonists. However, severe asthma escapes to usual treatments or frequently requires higher doses. In acute asthma, two main classes of bronchodilators are available: short actin beta-2 agonists and anticholinergics. These drugs are rapidly effective in general. However in some cases as acute severe asthma they can be insufficient, so that new drugs acting through other pathways to reverse airways obstruction could help preventing the still elevated number of asthma deaths. The pathophysiology of asthma must therefore be better understood in order to identify new targets and design new treatments.

The aim of the present invention is thus to provide new inhibitors of RAC1.

Another aim of the invention is to provide new compounds efficient for treating disorders of the airways, and especially for treating asthma.

Another aim of the invention is to provide RAC1 inhibitors useful for treating pathologies characterized by bronchoconstriction, such as asthma.

Thus, the present invention relates to a compound having the following formula (I):

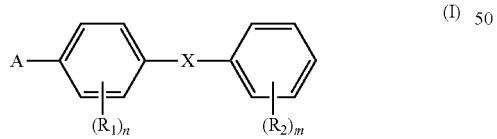

wherein:

A is chosen from the group consisting of:
- $-NR_aR_b$, $R_a$ and $R_b$, identical or different, being H or a $(C_1-C_6)$alkyl group, and preferably $NH_2$,
- $-NO_2$,
- $-N(CO-R_c)(CO-R'_c)$, $R_c$ and $R'_c$, identical or different, representing a $(C_2-C_6)$alkenyl group, or forming together with the carbon atoms carrying them and the nitrogen atom a heterocycloalkyl group comprising 5 to 10 atoms, and
- $-N(R'_a)-C(=O)-R$, and

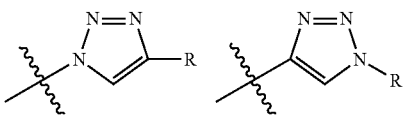

wherein:
  $R'_a$ is H or a $(C_1-C_6)$alkyl group, optionally substituted by at least one halogen atom, $R'_a$ being preferably H;
  R is chosen from the group consisting of:
    $(C_1-C_6)$alkyl groups, optionally substituted, for example by a halogen atom,
    $(C_2-C_6)$alkenyl groups,
    $(C_2-C_6)$alkynyl groups, optionally substituted by a group $-SiR_eR_fR_g$, $R_e$, $R_f$, and $R_g$ being, independently from each other, chosen from $(C_1-C_6)$alkyl groups, and
    groups having the following formula (II):

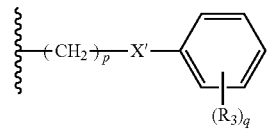

wherein:
    p is an integer comprised between 1 and 3,
    X' is chosen from the group consisting of: $-S-$, $-O-$, $-NH-$, $-NR_d-$, $-CH_2-$, $-SO_2-$, and $-SO-$, $R_d$ being H or a $(C_1-C_6)$alkyl group;
    q is 0 or is an integer comprised between 1 and 5, the $R_3$ groups, identical or different, are chosen from the group consisting of: $(C_1-C_6)$alkyl groups, halogen atoms, $(C_1-C_6)$alxoxy groups, $(C_1-C_6)$thioalkyl groups, and $-NR_aR_b$ groups, $R_a$ and $R_b$, identical or different, being H or a $(C_1-C_6)$alkyl group, and preferably $-NH_2$;
    $-CH_2-C(=O)-R$, wherein R is as defined above;
    $-N(R'_a)-SO_2-R$, wherein R and $R'_a$ are as defined above, $R'_a$ being preferably H;
    $-N(R'_a)-C(=O)-OR$, wherein R and $R'_a$ are as defined above, $R'_a$ being preferably H;
    $-N(R'_a)-C(=O)-N(R'_a)-R$, wherein R and $R'_a$ are as defined above, $R'_a$ being preferably H;
    $-N(R'_a)-SO_2-N(R'_a)-R$, wherein R and $R'_a$ are as defined above, $R'_a$ being preferably H;
X is chosen from the group consisting of:
    $-SO_2-N(R'_b)-$, $R'_b$ being H, a $(C_1-C_6)$alkyl group or a $-C(=O)-CH=CH_2$ group,
    $-N(R''_b)-SO_2-$, $R''_b$ being H or a $(C_1-C_6)$alkyl group,
    $-CO-NH-$,
    $-NH-CO-$,
    $-NH-CO-NH-$,
    $-NH-SO_2-NH-$,
    $-NH-CO-O-$,
    $-CO-O-$,
    $-HC=CH-$,
    $-C\equiv C-$,

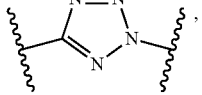 , 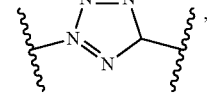 ,

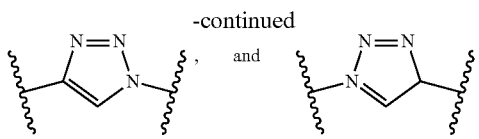

n is 0 or is an integer comprised between 1 and 4, the $R_1$ groups, identical or different, are chosen from the group consisting of: halogen atoms, $(C_1\text{-}C_6)$alkyl groups, $(C_1\text{-}C_6)$alxoxy groups, $(C_1\text{-}C_6)$thioalkyl groups, —$SCF_3$, —$SF_5$, and —$NR_aR_b$ groups, $R_a$ and $R_b$, identical or different, being H or a $(C_1\text{-}C_6)$alkyl group, and preferably —$NH_2$;

m is 0 or is an integer comprised between 1 and 5, the $R_2$ groups, identical or different, are chosen from the group consisting of: halogen atoms, $(C_1\text{-}C_6)$alkyl groups, $(C_1\text{-}C_6)$alkoxy groups, $(C_1\text{-}C_6)$thioalkyl groups, —$SCF_3$, —$SF_5$, and —$NR_aR_b$ groups, $R_a$ and $R_b$, identical or different, being H or a $(C_1\text{-}C_6)$alkyl group, and preferably —$NH_2$;

for use for the treatment of pathologies characterized by bronchoconstriction, such as asthma.

The present invention is thus based on the activity of inhibition of RAC1 of the compounds of formula (I).

The administration of the compounds of formula (I) is useful for inducing bronchodilation and preventing bronchospasm in mammals including humans.

Within the present application, the term "pathologies characterized by bronchoconstriction" refers to pathologies wherein bronchoconstriction occurs, that is to say a constriction of the airways in the lungs due to the tightening of surrounding smooth muscle, with consequent coughing, wheezing, and shortness of breath.

Among such pathologies, one may cite: asthma, chronic obstructive pulmonary disease (COPD), or cystic fibrosis.

According to a preferred embodiment, the present invention relates to a compound of formula (I) as defined above, for the treatment of asthma.

In the context of the present invention, the expression "$C_t$-$C_z$ ( . . . )" means a carbon-based chain which can have from t to z carbon atoms, for example $C_1$-$C_6$ means a carbon-based chain which can have from 1 to 6 carbon atoms.

Within the present application, the term "alkyl group" means: a linear or branched, saturated, hydrocarbon-based aliphatic group comprising, unless otherwise mentioned, from 1 to 6 carbon atoms. By way of examples, mention may be made of methyl, ethyl, n-propyl, isopropyl, butyl, isobutyl, tert-butyl or pentyl groups.

Within the invention, the term "alkenyl group" includes partially unsaturated, nonaromatic, hydrocarbon groups comprising, unless otherwise mentioned, from 2 to 6 carbon atoms.

Within the invention, the term "alkynyl group" means a nonaromatic, hydrocarbon group comprising at least one triple bond, and comprising, unless otherwise mentioned, from 2 to 6 carbon atoms.

Within the present invention, the term "heterocycloalkyl group" means: a 5- to 10-membered, saturated or partially unsaturated, monocyclic or bicyclic group comprising from one to three heteroatoms selected from 0, S or N.

Within the present invention, the term "alkoxy group" means: an —O-alkyl radical where the alkyl group is as previously defined. By way of examples, mention may be made of —O—$(C_1$-$C_4)$alkyl groups, and in particular the —O-methyl group, the —O-ethyl group as —O—$C_3$alkyl group, the —O-propyl group, the —O-isopropyl group, and as —O—$C_4$alkyl group, the —O-butyl, —O-isobutyl or —O-tert-butyl group;

Within the present invention, the term "halogen atom" means: a fluorine, a chlorine, a bromine or an iodine.

According to an embodiment, when X is —HC=CH—, then this double bond may be cis or trans.

According to an embodiment, in formula (I), when A represents a group —$N(CO-R_c)(CO-R'_c)$, $R_c$ and $R'_c$, identical or different, represent a $(C_2$-$C_6)$alkenyl group. Preferably, A represents a group —$N(CO-CH=CH_2)_2$.

According to another embodiment, in formula (I), when A represents a group —$N(CO-R_c)(CO-R'_c)$, $R_c$ and $R'_c$, identical or different, form together with the carbon atoms carrying them and the nitrogen atom a heterocycloalkyl group comprising 5 to 10 atoms. According to this embodiment, A may thus represent a group derived from maleimide or phtalimide.

According to an embodiment, in formula (I), when A represents a group —$N(R'_a)$—$C(=O)$—R, $R'_a$ is preferably H. According to this embodiment, R is preferably a group of formula (II) as defined above. Preferably, in formula (II), X' is —S—, —O— or —$CH_2$—, and is more preferably —S—.

Preferably, in formula (II), q is 0, 1 or 2.

Preferably, in formula (II), $R_3$ is an alkyl group such as methyl, especially p-Me.

According to a preferred embodiment, in formula (I), A is preferably chosen from the group consisting of: —$NH_2$, —$NO_2$, —$N(CO-CH=CH_2)_2$, and —$N(R'_a)$—$C(=O)$—R, $R'_a$ and R being as defined above.

According to a preferred embodiment, in formula (I), A is preferably chosen from the group consisting of: —$NH_2$, —$NO_2$, —$N(CO-CH=CH_2)_2$, and —NH—$C(=O)$—R, R being as defined above.

A preferred subgroup of compounds used according to the invention is constituted by compounds having the following formula (III):

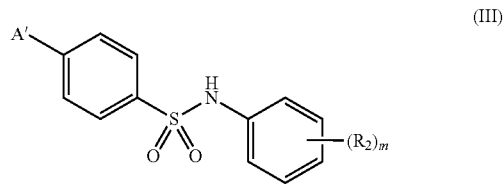

(III)

wherein:

A' is $NO_2$ or $NH_2$; and m and $R_2$ are as defined above in formula (I).

The compounds of formula (III) correspond to compounds of formula (I) as defined above wherein A is $NO_2$ or $NH_2$, n=0, and X is —$SO_2$—NH—.

Preferably, in formula (III), m is 1 or 2.

Preferably, in formula (III), the $R_2$ groups, which may be identical or different, are chosen from alkoxy groups.

According to an embodiment, in formula (III), $R_2$ is a methoxy group. Preferably, when m=1, $R_2$ is a methoxy group in ortho or meta position. Preferably, when m=2, the $R_2$ groups are methoxy groups in 2- and 5-positions.

Another preferred subgroup of compounds used according to the invention is constituted by compounds having the following formula (IV):

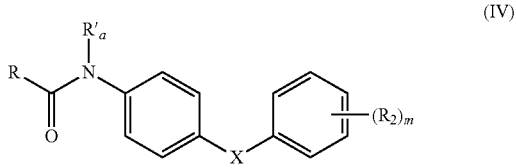

wherein R, R'$_a$, X, m, and R$_2$ are as defined above in formula (I).

The compounds of formula (IV) correspond to compounds of formula (I) as defined above wherein A is —N(R'$_a$)—C(=O)—R, and n=0.

According to an embodiment, in formula (IV), R'$_a$ is H. According to an embodiment, in formula (IV), R is a group of formula (II) as defined above. Preferably, in formula (II), X' is —S—, —O— or —CH$_2$—, and is more preferably —S—. Preferably, in formula (II), q is 0, 1 or 2. Preferably, in formula (II), R$_3$ is an alkyl group such as methyl, especially p-Me.

Another preferred subgroup of compounds used according to the invention is constituted by compounds having the following formula (V):

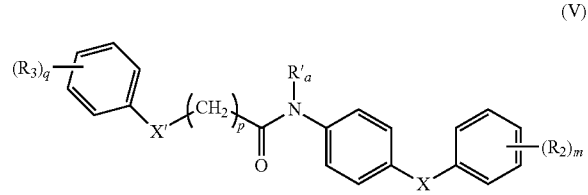

wherein R'$_a$, X, X', p, q, m, R$_2$ and R$_3$ are as defined above in formula (I).

The compounds of formula (V) correspond to compounds of formula (IV) as defined above wherein R is a group of formula (II) as defined above.

According to an embodiment, in formula (V), R'$_a$ is H. Preferably, for compounds of formula (V), X' is —S—, —O— or —CH$_2$—, and is more preferably —S—.

Preferably, in formula (V), q is 0, 1 or 2.

Preferably, in formula (V), R$_3$ is an alkyl group such as methyl, especially p-Me.

Preferably, in formula (V), m is 1 or 2, and the R$_2$ groups are chosen from the alkyl and alkoxy groups.

Another preferred subgroup of compounds used according to the invention is constituted by compounds having the following formula (VI):

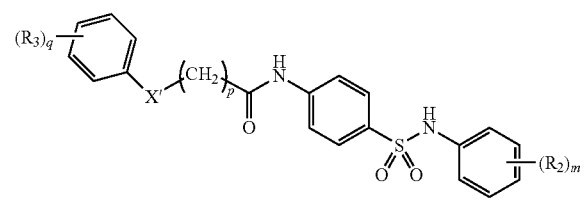

wherein X', p, q, m, R$_2$ and R$_3$ are as defined above in formula (I).

The compounds of formula (VI) correspond to compounds of formula (V) as defined above wherein R'$_a$ is H and X is —SO$_2$—NH—.

Preferably, in formula (VI), q=0 or 1, and the R$_3$ groups are chosen from the alkyl groups as defined above.

Preferably, in formula (VI), X' is —CH$_2$— or —S—.

Preferably, in formula (VI), m=1 or 2, and the R$_2$ groups are chosen from the alkyl and alkoxy groups as defined above.

Another preferred subgroup of compounds used according to the invention is constituted by compounds having the following formula (VII):

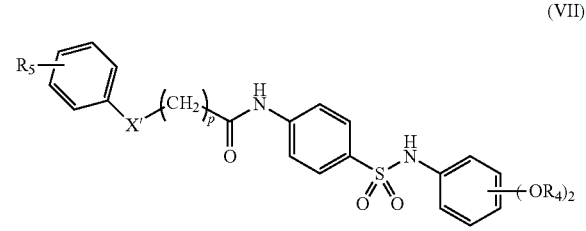

wherein:
X' and p are as defined above in formula (I);
R$_5$ is a (C$_1$-C$_6$)alkyl group; and
the R$_4$ groups, identical or different, are chosen from the (C$_1$-C$_6$)alkyl groups.

Preferably, in formula (VII), X' is —CH$_2$— or —S—.

The present invention also relates to the compounds having the following formula (I) as defined above as such. It also relates to the compounds having one of the formulae (III), (IV), (V), (VI), and (VII) as such, said formulae being as defined above.

As preferred compounds used according to the invention, one may mention the followings:

(1)

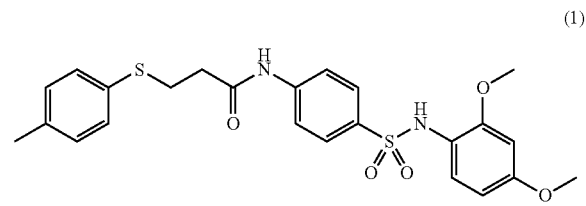

(2)

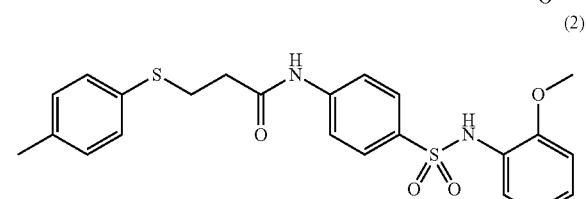

(3)

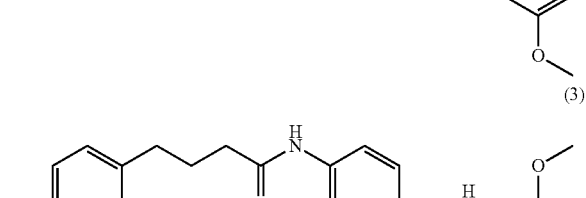

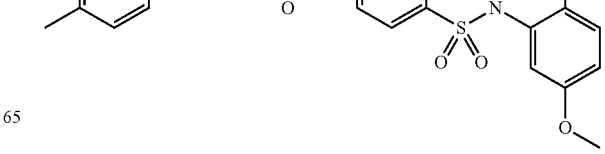

(4)
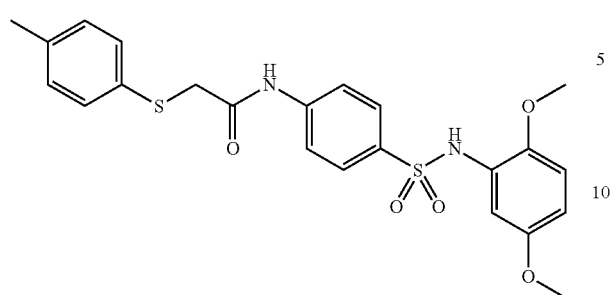
(5)
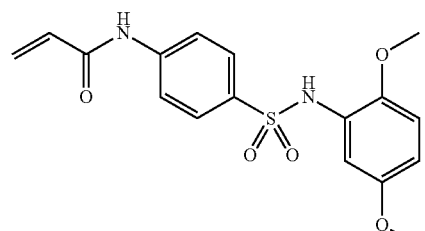
(6)
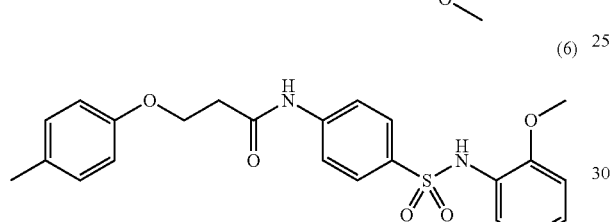
(7)
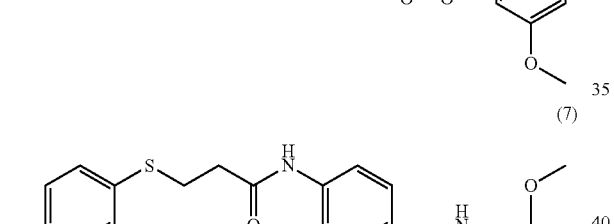
(8)
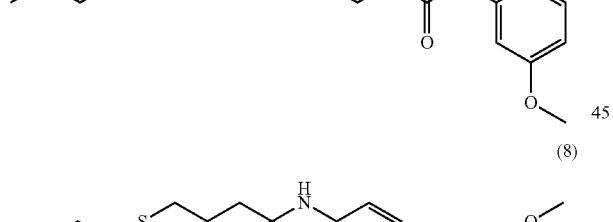
(9)
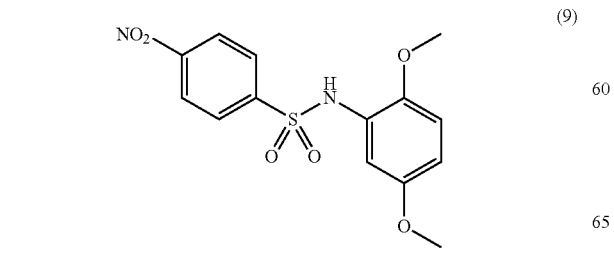
(10)
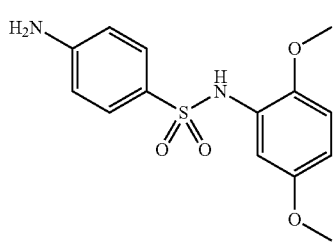
(11)
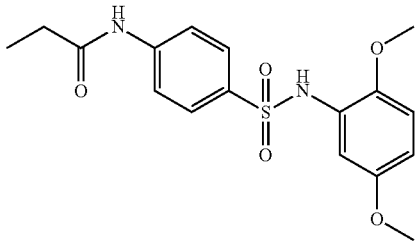
(12)
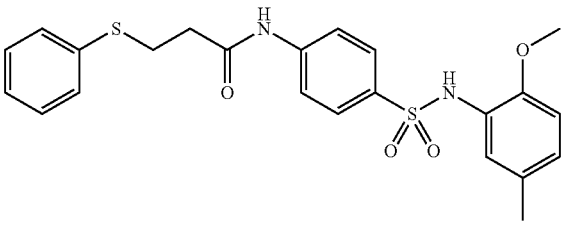
(13)
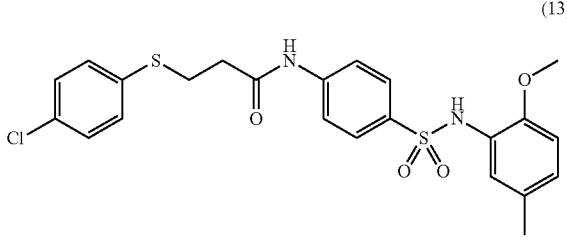
(14)
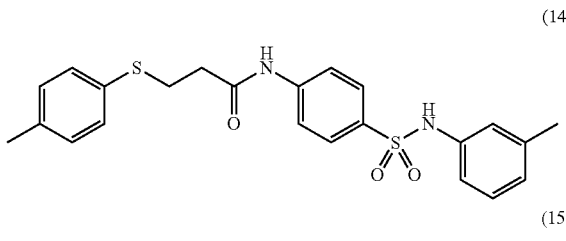
(15)
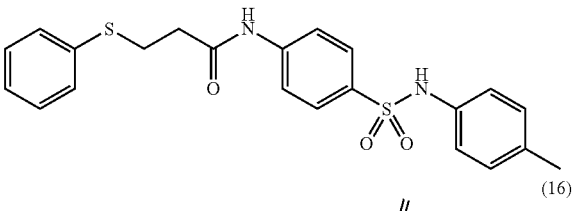
(16)
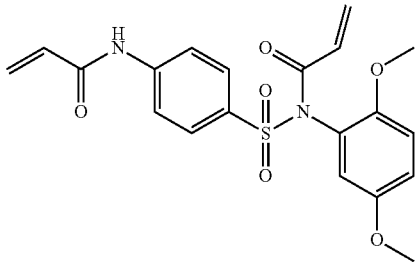

(17)
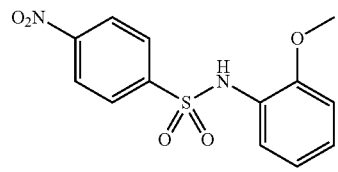
(18)
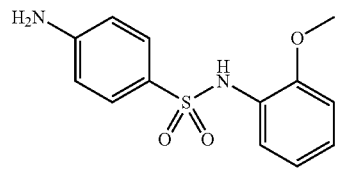
(19)
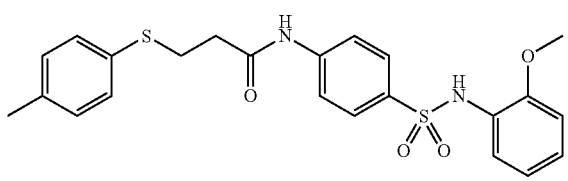
(20)
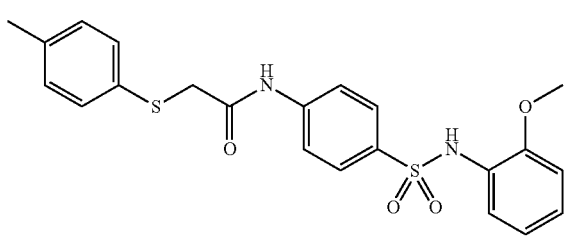
(21)
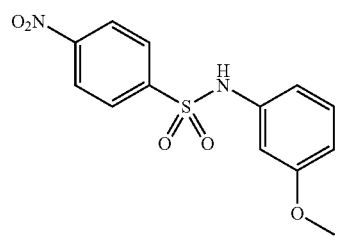
(22)
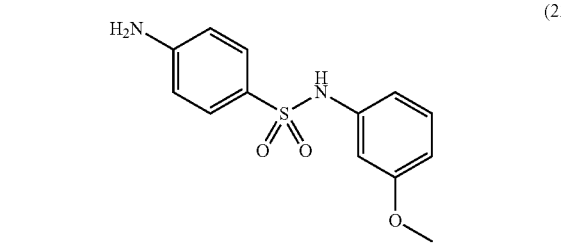
(23)
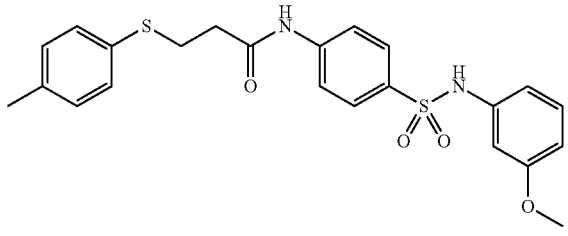
(24)
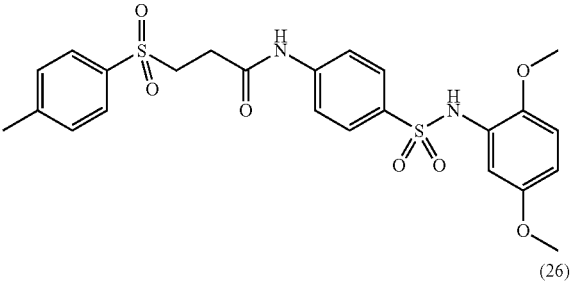
(25)
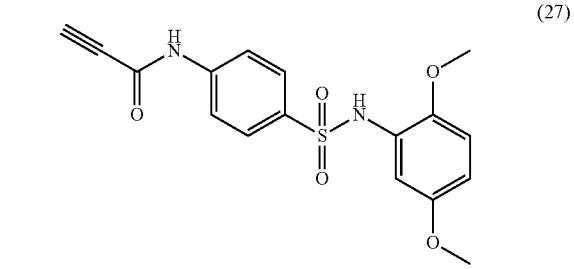
(26)
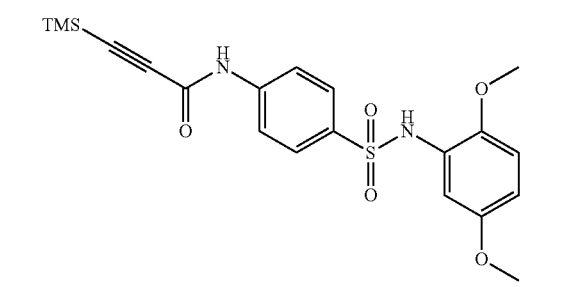
(27)
(28)
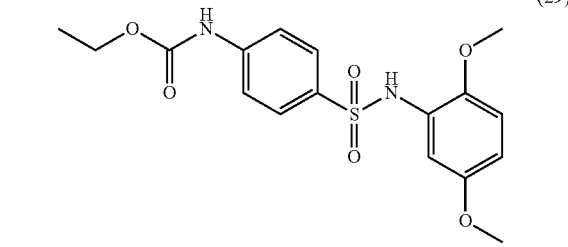
(29)

-continued (30)

(31)

As preferred compounds as such, one may mention the followings: (3), (4), (5), (6), (7), (8), (9), (10), (11), (16), (17), (18), (19), (20), (21), (22), (23), (24), (25), (26), (27), (28), (29), (30), and (31).

The present invention also relates to a medicament comprising a compound as defined above, in particular a compound having one of the formulae (I), (Ill), (IV), (V), (VI) or (VII).

The present invention also relates to a pharmaceutical composition, comprising a compound as defined above, in particular a compound having one of the formulae (I), (Ill), (IV), (V), (VI) or (VII), and at least one pharmaceutically acceptable excipient.

These pharmaceutical compositions contain an effective dose of at least one compound according to the invention, or a pharmaceutically acceptable salt, and also at least one pharmaceutically acceptable excipient.

Said excipients are selected, according to the pharmaceutical form and the mode of administration desired, from the usual excipients which are known to those skilled in the art.

EXAMPLES

Preparation of Compounds of Formula (I)

One embodiment of the present invention relates to sulfonamides compounds represented by the following schemes.

As representative examples of these series, the synthesis of sulfonamides derivatives proceeds toward the functionalization of various terminal aniline compounds as shown in scheme 1. The sulfonamide was introduced by reaction of primary aniline with the appropriate p-nitrobenzenesulfonyl chloride under basic conditions as shown in scheme 1. Further reduction of the nitro group in presence of iron gives access to anilines bearing the sulfonamide moieties. Then, finally, the acylation of the resulting primary aniline with the appropriate acyl chloride affords the expected derivatives similar to one of those depicted in formula (VI).

Scheme 1

$R_1$ = OMe; $R_2$ = OMe; $R_3$ = H
$R_1$ = OMe; $R_2$ = H; $R_3$ = OMe
$R_1$ = OMe; $R_2$ = H; $R_3$ = H
$R_1$ = H; $R_2$ = H; $R_3$ = OMe
$R_1$ = F; $R_2$ = H; $R_3$ = H

Fe (3 equiv.)
NH$_4$Cl (5 equiv.)
MeOH

Pyridine
DCM (9) $R_1$ = OMe; $R_2$ = H; $R_3$ = OMe
(17) $R_1$ = OMe; $R_2$ = H; $R_3$ = H
(21) $R_1$ = H; $R_2$ = H; $R_3$ = OMe

(10) $R_1$ = OMe; $R_2$ = H; $R_3$ = OMe
(18) $R_1$ = OMe; $R_2$ = H; $R_3$ = H
(22) $R_1$ = H; $R_2$ = H; $R_3$ = OMe

ClCOCOCl
DCM
DMF

Organic Base
DCM

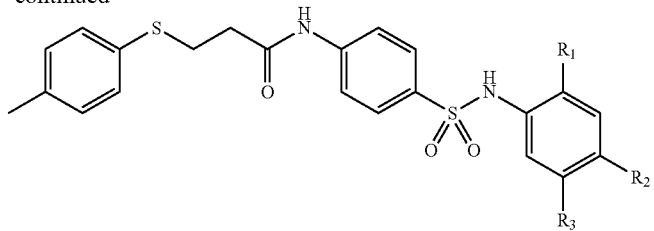

(1) $R_1$ = OMe; $R_2$ = OMe; $R_3$ = H
(2) $R_1$ = OMe; $R_2$ = H; $R_3$ = OMe
(19) $R_1$ = OMe; $R_2$ = H; $R_3$ = H
(23) $R_1$ = H; $R_2$ = H; $R_3$ = OMe
(30) $R_1$ = F; $R_2$ = H; $R_3$ = H

Another embodiment of the present invention relates to another subgroup of compounds featuring varied functional groups of the terminal amides of the sulfonamides. Scheme 2 shows representative examples of these modifications. The synthesis starts from substituted primary anilines (as shown for instance with compound (10) in scheme 2) that are previously obtained via the formation of sulfonamides. The acylation reaction is performed under basic conditions in presence of various acyl chlorides derivatives.

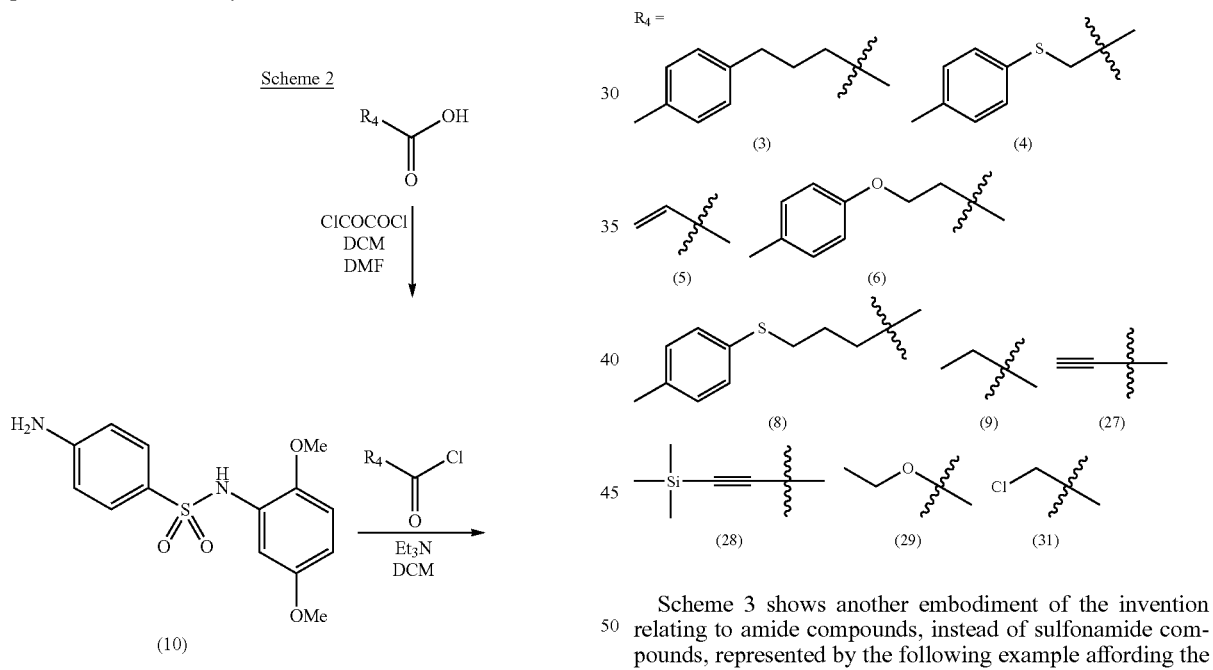

Scheme 3 shows another embodiment of the invention relating to amide compounds, instead of sulfonamide compounds, represented by the following example affording the compound (7).

Scheme 3

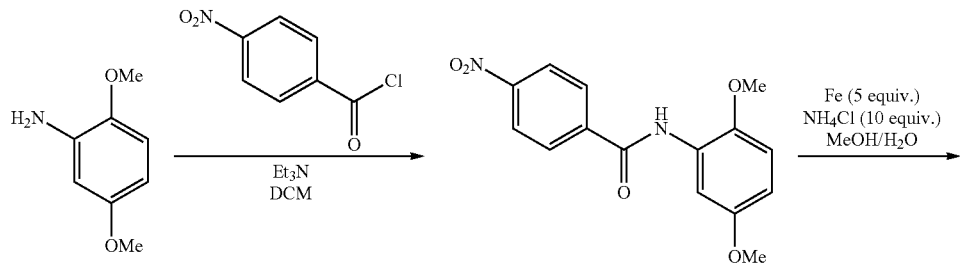

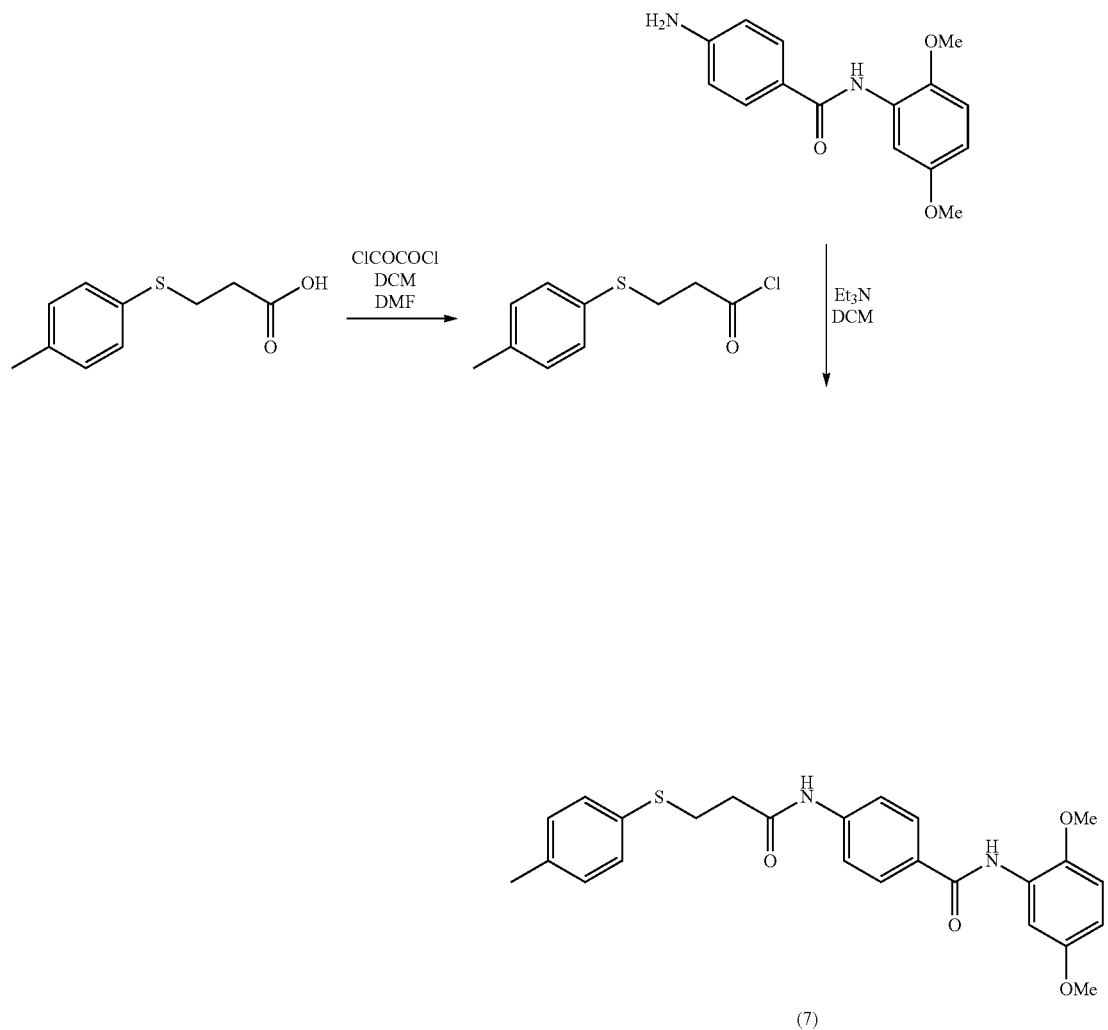
Scheme 4 shows the synthesis of an example of sulfonamide derivative combining variations of the initial aromatic ring of compound (2) and modification of its initial acylating reagent. This synthesis involves the acylation of the primary aniline under standard conditions.
Scheme 4
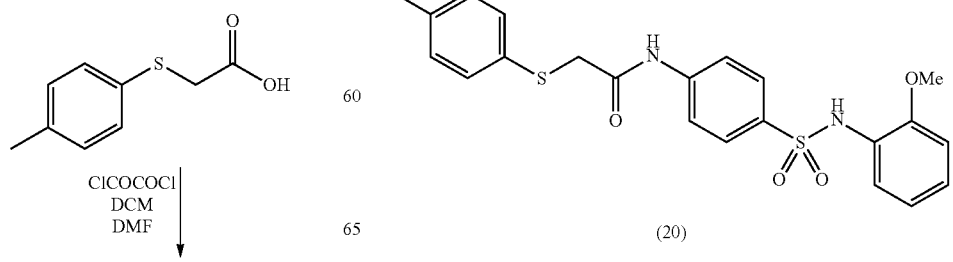

Scheme 5 and Scheme 6 show representative examples for the synthesis of sulfoxides and sulfones compounds arising from the original sulfonamides subgroup basic conditions of the nitrobenzene sulfonamide derivatives. After subsequent reduction of the nitro group and acylation of the resulting primary anilines, these chemical

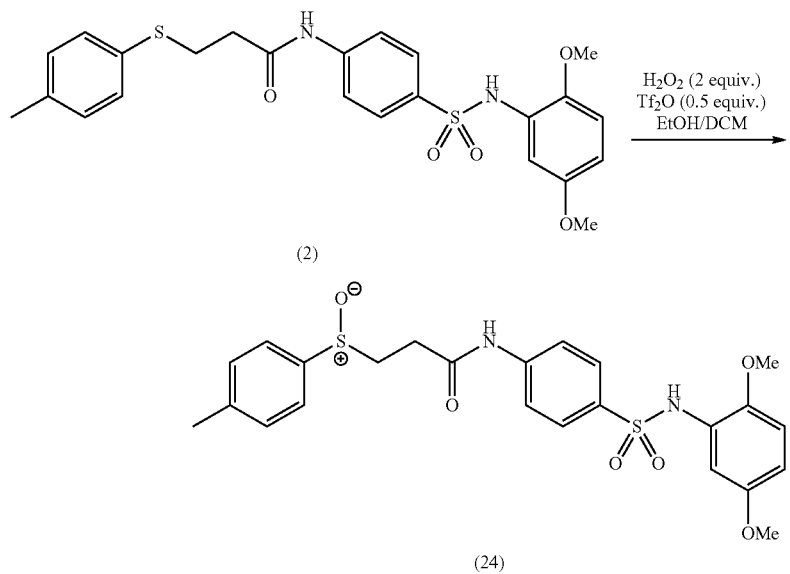

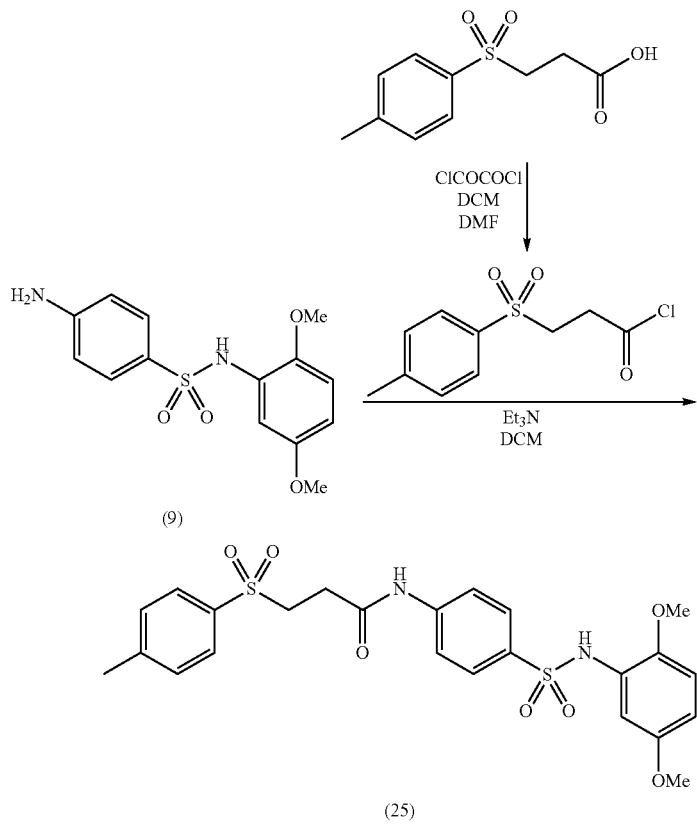

As another representative examples of the embodiment, schemes 7 and 8 present sulfonamides bearing additional functional groups on nitrogen atoms. Functionalization of the free NH of sulfonamide is obtained by alkylation under transformations give access to N-disubstituted sulfonamides as depicted with the example (26) in scheme 7. Functionalization of the free NH of sulfonamide is also obtained under acylation conditions as depicted in scheme 8.

Scheme 7

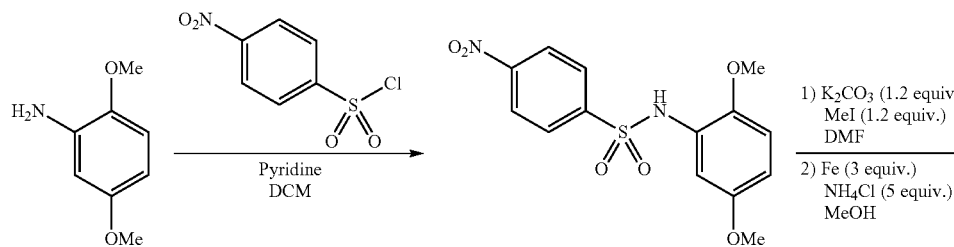

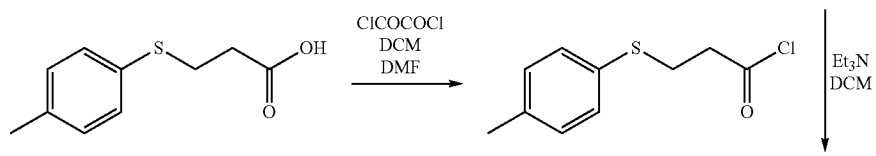

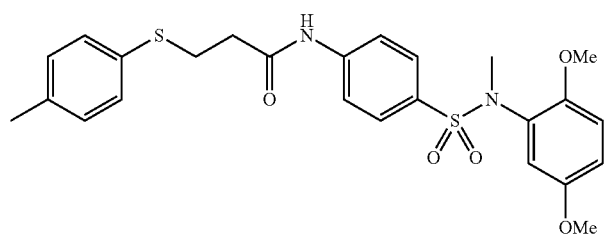

(26)

Scheme 8

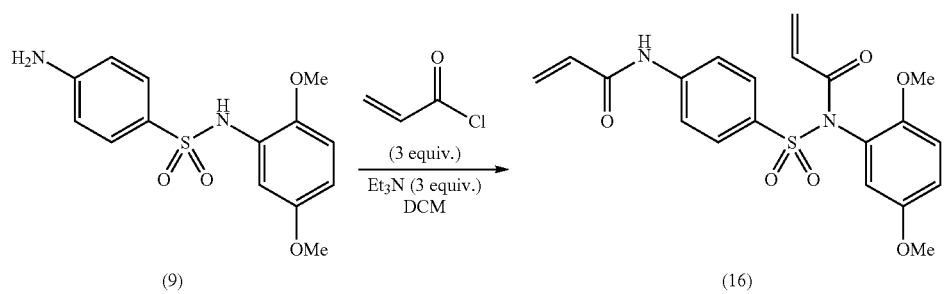

(9)  (16)

General Experimental Details

Solvents were purified and dried by standard methods prior to use; alternatively, the MB SPS—800-dry solvent system was used to dry dichloromethane. Commercially available reagents were purchased from Sigma Aldrich and were used without purification. Dry dichloromethane was obtained by refluxing solvent on calcium hydride for an hour and distilled under argon. Glassware used for reaction was either flame dried under vacuum or under argon stream for several minutes. Reactions were carried out under rigorous anhydrous conditions and argon stream/positive pressure of argon. $^1$H and $^{13}$C NMR spectra were recorded on a Bruker Avance 300 spectrometer fitted with a 5 mm i.d. BBO probe carefully tuned to the recording frequency of 300.13 MHz (for $^1$H) and 75.47 MHz (for $^{13}$C), the temperature of the probe was set at room temperature (around 293-294 K), on a Bruker Avance 400 spectrometer fitted with a 5 mm i.d. BBFO+ probe carefully tuned to the recording frequency of 400.13 MHz (for $^1$H) and 100.61 MHz (for $^{13}$C). The spectra are referenced to the solvent in which they were run (7.26 ppm for $^1$H CDCl$_3$ and 77.16 ppm for $^{13}$C CDCl$_3$, 2.5 ppm for $^1$H DMSO and 39.52 ppm for $^{13}$C DMSO). Chemical shifts (δ) are given in ppm, and coupling constants (J) are given in Hz with the following splitting abbreviations: s=singlet, d=doublet, t=triplet, q=quartet, qt=quintet, sx=sextuplet, sp=septuplet, m=massif and br=broad. All assignments were confirmed with the aid of two-dimensional $^1$H, $^1$H (COSY), or $^1$H, $^{13}$C (HSQC, HMBC) experiments using standard pulse programs. All reactions were monitored by TLC on commercially available precoated plates (Kieselgel 60 F254), and the compounds were visualized with KMnO$_4$ solution [KMnO$_4$ (3 g), K$_2$CO$_3$ (20 g), NaOH (5% aq.; 5 mL), H$_2$O (300 mL)] and heating or by UV (254 nm) when possible. Flash column chromatography was carried out using high purity grade (Merck grade 9385) pore size 60 Å, 230-400 mesh particle size silica gel (Sigma Aldrich). Solvents used for chromatography were prior distilled on a Buchi rotavapor R-220-SE. Low resolution mass spectrometry (MS) were recorded on a ThermoFinnigan DSQII quadripolar spectrometer (coupled with a Trac-Ultra GC apparatus) for Chemical Ionization (CI), on a ThermoFinnigan LCQ Advantage spectrometer for Electro-Spray Ionisation (ESI). High resolution mass spectrometry (HRMS) were recorded on a ThermoFinnigan MAT95XL spectrometer (for CI) and on a Thermo Fisher Scientific LTQ-Orbitrap spectrometer (for ESI).

Example 1:
N-(2,4-dimethoxyphenyl)-4-nitrobenzenesulfonamide

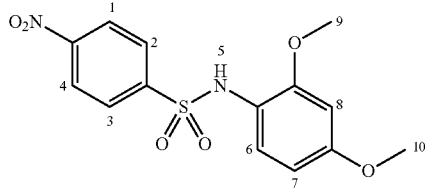

To a solution of 2,4-dimethoxyaniline (4.87 g, 31.59 mmol) dissolved in dried DCM (175 mL) was added pyridine (2.56 mL, 31.59 mmol). The 4-nitrobenzenesulfonyl chloride (7 g, 31.59 mmol), also dissolved in dried DCM, was added dropwise. After 24 hours of stirring at room temperature, the reaction mixture was quenched with water. After extraction with DCM, the organic layers were washed with aqueous solution of 10% K$_2$CO$_3$, followed by aqueous saturated solution of NaCl. After drying with MgSO$_4$, the crude was obtained by filtration and concentration under vacuum. The crude mixture was purified by chromatography over a silica gel column (PE/AcOEt: 7/3) and afforded the expected N-(2,4-dimethoxyphenyl)-4-nitrobenzenesulfonamide (7.8 g, 23 mmol) as a light brown solid with 78% yield. (Rf=0.82 (EP/EtOAc: 1/1)); mp=161° C. RMN $^1$H (300 MHz, CDCl$_3$): 8.22 (d, 2H, H$^1$—H$^4$), 7.84 (d, 2H, H$^2$—H$^3$), 7.46 (d, 1H, H$^8$), 6.66 (s, 1H, H$^5$), 6.47 (dd, 1H, H$^7$), 6.27 (d, 1H, H$^6$), 3.77 (s, 3H, H$^{10}$), 3.47 (s, 3H, H$^9$). RMN $^{13}$C (75 MHz, CDCl$_3$): 159.2 (C$^{IV}$), 152.1 (C$^{IV}$), 150.0 (C$^{IV}$), 144.9 (C$^{IV}$), 128.6 (C$^2$—C$^3$), 125.7 (C$^8$), 123.7 (C$^1$—C$^4$), 117.2 (C$^{IV}$), 104.6 (C$^7$), 98.7 (C$^6$), 55.5 (CH$_3$), 55.4 (CH$_3$). HRMS: Calculated for [M+Na]$^+$ 361.0470; Measured: 361.0470. IR: 3269 (v N—H), 3109 (v Car-H), 2840 (v OC—H), 1523 (v$_{as}$ NO$_2$), 1352 (v$_s$ NO$_2$), 128 (v$_{as}$ SO$_2$), 1159 (v$_s$ SO$_2$).

Example 2:
N-(2,5-dimethoxyphenyl)-4-nitrobenzenesulfonamide (9)

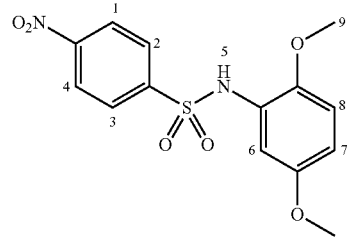 [SMILES: COc1ccc(OC)c(NS(=O)(=O)c2ccc([N+](=O)[O-])cc2)c1]

To a solution of 2,5-dimethoxyaniline (4.87 g, 31.59 mmol) in DCM (175 mL) were subsequently added dropwise pyridine (2.56 mL, 31.59 mmol) and a solution of 4-nitrobenzenesulfonyl chloride (7 g, 31.59 mmol) in DCM. After 24 hours of stirring at room temperature, the reaction mixture was quenched with H$_2$O. After extraction three times with DCM, the organic layer was washed with an aqueous solution of 10% K$_2$CO$_3$, and a saturated aqueous solution of NaCl. After drying with MgSO$_4$, filtration and concentration under vacuum, the crude was purified by chromatography over silica gel (PE/AcOEt: 7/3) and afforded the expected compound (9) as a yellow solid (7.8 g, 23 mmol) with 78% yield. (Rf=0.88 (EP/EtOAc: 1/1)); mp=165° C. RMN $^1$H (300 MHz, CDCl$_3$): 8.24 (d, 2H, H$^1$—H$^4$), 7.94 (d, 2H, H$^2$—H$^3$), 7.17 (d, 1H, H$^6$), 7.06 (s, 1H, H$^5$), 6.67 (dd, 1H, H$^8$), 6.61 (d, 1H, H$^7$), 3.77 (s, 3H, CH$_3$), 3.59 (s, 3H, CH$_3$). RMN $^{13}$C (75 MHz, CDCl$_3$): 159.0 (C$^{IV}$), 150.2 (C$^{IV}$), 144.8 (C$^{IV}$), 143.9 (C$^{IV}$), 128.5 (C$^2$—C$^3$), 125.4 (C$^{IV}$), 124.0 (C$^1$—C$^4$), 111.5 (C$^8$), 110.8 (C$^7$), 108.3 (C$^6$), 56.7 (CH$_3$), 55.8 (CH$_3$). HRMS: Calculated for [M+Na]$^+$361.0470; Measured: 361.0470. IR: 3310 (v N—H), 3107 (v Car-H), 2841 (v OC—H), 1534 (v$_{as}$ NO$_2$), 1391 (v$_s$ NO$_2$), 1345 (v$_{as}$ SO$_2$), 1157 (v$_{as}$ NO$_2$)

Example 3:
N-(2-methoxyphenyl)-4-nitrobenzenesulfonamide (17)

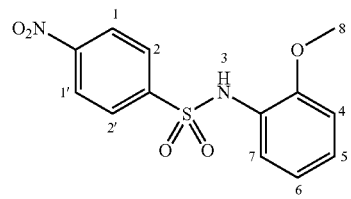

To a solution of o-anisidine (2 mL, 15 mmol) in DCM (40 mL) were subsequently added dropwise dry pyridine (1.15 mL, 15 mmol) and a solution of 4-nitrobenzenesulfonyl chloride (3.32 g, 15 mmol) in DCM (40 mL). After 24 hours of stirring at room temperature, the reaction mixture was quenched with H$_2$O (80 mL). After extraction three times with DCM, the organic layer was washed with an aqueous solution of 10% $K_2CO_3$ (60 mL), and a saturated aqueous solution of NaCl (60 mL). After drying with $MgSO_4$, filtration and concentration under vacuum, the crude was purified by chromatography over silica gel (PE/EtOAc: 90/10 to 0/100) affording the expected compound (17) as a yellow solid (4.28 g, 13.9 mmol) with 93% yield. ((Rf=0.74 (PE/EtOAc: 7/3), mp=156.5° C.)$^1$H NMR (300 MHz, $CDCl_3$) δ 8.23 (dt, $J_{2-2'}$=2.1 Hz, $J_{2-1}$=9.0 Hz, 2H, $H_2$ and $H_{2'}$), 7.91 (dt, $J_{1-1'}$=2.1 Hz, $J_{1-2}$=9.0 Hz, 2H, $H_1$ and $H_{1'}$), 7.55 (dd, $J_{7-5}$=1.6 Hz, $J_{7-6}$=7.8 Hz, 1H, $H_7$), 7.10 (dt, $J_{6-4}$=1.6 Hz, $J_{6-7}$=7.8 Hz, 1H, $H_6$), 7.04 (bs, 1H, $H_3$), 6.94 (dt, $J_{6-4}$=1.2 Hz, $J_{5-4}$=7.8 Hz, 1H, $H_5$), 6.74 (dd, $J_{4-5}$=7.8 Hz, 1H, $H_4$), 3.62 (s, 3H, $H_8$)$^{13}$C NMR (75 MHz, $CDCl_3$) δ 150.3, 150.0, 145.0 ($C^{IV}$ Ar) 128.6 ($C_2$ and $C_{2'}$), 126.7 ($C_6$), 124.0 ($C_1$ and $C_{1'}$), 122.3 ($C_7$), 121.4 ($C_5$), 110.9 ($C_4$), 77.4 ($C^{IV}$ Ar) 55.7 (C8) MS (EI, m/z): [M$^{+\bullet}$]=308.0 HRMS: Calculated for [M+Na]$^+$331.0356; Measured: 331.0359. IR (cm$^{-1}$): 3244 (vNH), 3100 (v=C—H), 1525 (v $NO_2$), 1310 ($v_{as}$ $SO_2$).

Example 4:
N-(3-methoxyphenyl)-4-nitrobenzenesulfonamide (21)

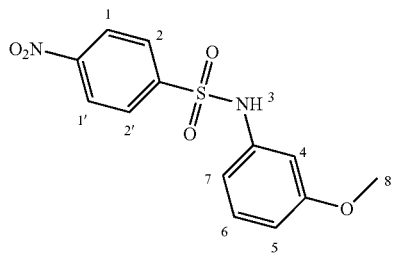

To a solution of m-anisidine (2 ml, 15 mmol) in DCM (40 mL) were subsequently added dropwise dry pyridine (1.15 mL, 15 mmol) and a solution of 4-nitrobenzenesulfonyl chloride (4.54 g, 14.6 mmol) in DCM (40 mL). After 24 hours of stirring at room temperature, the reaction mixture was quenched with $H_2O$ (80 mL). After extraction three times with DCM, the organic layer was washed with an aqueous solution of 10% $K_2CO_3$ (60 mL), and a saturated aqueous solution of NaCl (60 mL). After drying with $MgSO_4$, filtration and concentration under vacuum, the crude was purified by chromatography over silica gel (PE/EtOAc: 90/10 to 0/100) affording the expected compound (21) as a yellow solid (4.53 g, 14.7 mmol) with 98% yield. (Rf=0.58 (PE/EtOAc: 5/5); mp=119.4° C.). $^1$H NMR (300 MHz, $CDCl_3$): δ 8.27 (dt, $J_{2-2'}$=2.1 Hz, $J_{2-1}$=9.0 Hz, 2H, $H_2$ and $H_{2'}$), 7.97 (dt, $J_{1-1'}$=2.1 Hz, $J_{1-2}$=9.0 Hz, 2H, $H_1$ and $H_{1'}$), 7.15 (m, 1H, $H_7$), 7.09 (s, 1H, $H_3$), 6.69 (m, 2H, $H_4$ and $H_6$), 6.62 (m, 1H, $H_5$), 3.75 (s, 3H, $H_8$)$^{13}$C NMR (75 MHz, $CDCl_3$) δ 160.6, 150.4, 144.6, 136.7 ($C^{1''}$ Ar) 130.6 ($O_7$), 128.7 ($C_1$ and $C_{1'}$), 124.4 ($C_2$ and $C_{2'}$), 114.0 ($C_5$), 121.5 ($C_5$), 111.7, 108.1 ($O_4$ and $O_6$), 55.5 ($O_8$) MS (EI, m/z): [M$^{+\bullet}$]=308.0 HRMS: Calculated for [M+H]$^+$ 309.0537; Measured: 309.0540. IR (cm$^{-1}$): 3245 (vNH), 3113 (v=C—H), 1528 (v $NO_2$), 1306 ($v_{as}$ $SO_2$)

Example 5:
N-(2,4-dimethoxyphenyl)-4-nitrobenzenesulfonamide

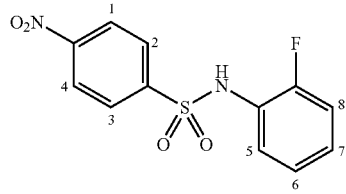

To a solution of 4-fluoroaniline (15 mmol, 1.45 mL) dissolved in dry DCM (60 mL) were added dropwise pyridine (15 mmol, 1.15 mL) and the 4-nitrobenzene-1-sulfonyl chloride (15 mmol, 3.32 g) dissolved in dry DCM. After stirring at room temperature over 24 hours, the reaction mixture was quenched with water. The aqueous layer was extracted twice with DCM. The combined organic layers were washed with $H_2O$, then an aqueous solution of 10% $K_2CO_3$, and an aqueous saturated solution of NaCl. After drying with $MgSO_4$, filtration and concentration under vacuum, the crude was purified by chromatography over silica gel (pure DCM) affording N-(2,4-dimethoxyphenyl)-4-nitrobenzenesulfonamide (3.3 g; 11.15 mmol) with 75% yield (Rf=0.53 (DCM 100%); mp=166° C.). RMN $^1$H (300 MHz, $CDCl_3$): 8.29 (d, 2H, H$^1$—H$^4$), 7.94 (d, 2H, H$^2$—H$^3$), 7.55-7.65 (m, 1H, H$^6$), 7.10-7.17 (m, 2H, H$^5$—H$^7$), 6.92-7.15 (m, 1H, H$^8$), 6.80 (s, 1H, NH). RMN $^{13}$C (75 MHz, $CDCl_3$): [153.0-156.3] (C—F), 150.6 ($C^V$), 144.6 ($C^V$), 128.6 ($C^2$—$C^3$), [127.7-127.8] (Car), [125.2-125.3] (Car), 124.8 ($C^6$), 124.5 ($C^1$—$C^4$), [123.4-123.6] ($C^V$), [115.8-116.0] ($C^8$). HRMS: Calculated for [M+Na]+319.0173; Measured: 319.0165. IR (cm$^{-1}$): 3259 (vNH), 1604, 1519 (v $NO_2$), 1341 ($v_{as}$ $SO_2$); 1309; 1160.

Example 6:
4-amino-N-(2,4-dimethoxyphenyl)benzenesulfonamide

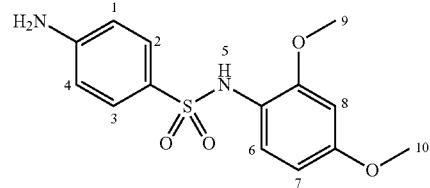

To a solution of N-(2,4-dimethoxyphenyl)-4-nitrobenzenesulfonamide (2 g, 6.48 mmol) in MeOH were successively added iron (1.06 g, 19 mmol) and an aqueous solution of $NH_4Cl$ (1.72 g, 32.46 mmol in 20 mL of $H_2O$). After stirring over 60 hours at 70° C., the reaction mixture was filtered through a pad of celite on sintered funnel. After successive washings with acetone, DCM and ethyl acetate, the biphasic mixture was separated. The aqueous layer was extracted twice with DCM. The combined organic layers were dried over $MgSO_4$ and the solvents were concentrated under vacuum. The crude was purified by chromatography over silica gel (PE/EtOAc: 1/1) affording the expected compound as a light brown solid (1.37 g, 4.44 mmol) with 68% yield. (Rf: 0.22 (EP/EtOAc: 1/1); mp: 115° C.). RMN $^1$H (300

MHz, CDCl$_3$): 7.41 (d, 2H, H$^2$—H$^3$), 7.37 (d, 1H, H$^8$), 6.562 (s, 1H, H$^5$), 6.537 (d, 2H, H$^1$—H$^2$), 6.420 (dd, 1H, H$^8$), 6.280 (d, 1H, H$^6$), 3.754 (s, 3H, H$^{10}$), 3.534 (s, 3H, H$^9$). RMN $^{13}$C (75 MHz, CDCl$_3$): 158.153 (C$^6$), 151.798 (C$^5$), 150.448)(C$^0$, 129.404 (C3-C4), 127.423 (C$^4$), 124.273 (C$^7$), 119.209 (C$^5$), 113.601 (C$^1$—C$^2$), 104.216 (C$^8$), 98.756 (C$^6$), 55.533 (C$^{10}$), 55.487 (C$^9$) HRMS: Calculated for [M+Na]$^+$ 331.0728; Measured: 331.0723. IR: 3362 (v$_{as}$ NH$_2$), 2937 (v Car-H), 2837 (v OC—H), 1590 (δ NH$_2$), 1207 (v Csp$^2$-O-Csp$^3$)

Example 7:
4-amino-N-(2,5-dimethoxyphenyl)benzenesulfonamide (10)

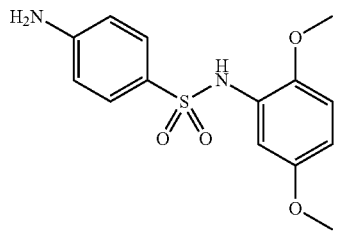

To a solution of N-(2,5-dimethoxyphenyl)-4-nitrobenzenesulfonamide (2 g, 6.48 mmol) in MeOH were successively added iron (1.06 g, 19 mmol) and an aqueous solution of NH$_4$Cl (1.72 g, 32.46 mmol in 20 mL of H$_2$O). After stirring over 60 hours at 70° C., the reaction mixture was filtered through a pad of celite on sintered funnel. After successive washings with acetone, DCM and ethyl acetate, the biphasic mixture was separated. The aqueous layer was extracted twice with DCM. The combined organic layers were dried over MgSO$_4$ and the solvents were concentrated under vacuum. The crude was purified by chromatography over silica gel (PE/EtOAc: 1/1) affording the expected compound (10) as a light brown solid (1.4 g, 4.54 mmol) with 70% yield. (Rf: 0.36 (EP/EtOAc: 1/1); mp: 126° C.). RMN $^1$H (300 MHz, CDCl$_3$): 7.55 (d, 2H, H$^2$—H$^3$), 7.10 (d, 1H, H$^6$), 6.99 (s, 1H, H$^5$), 7.65 (d, 2H, H$^8$), 6.56 (d, 1H, H$^2$—H$^4$), 6.51 (m, 1H, H$^6$), 3.73 (s, 3H, CH$_3$), 3.63 (s, 3H, CH$_3$). RMN $^{13}$C (75 MHz, CDCl$_3$): 154.1 (CO), 151.0 (CO), 143.6 (C$^{IV}$), 130.0 (C$^2$—C$^3$), 127.5 (C$^{IV}$), 127.4 (C$^{IV}$), 112.0 (C$^1$—C$^4$), 111.7 (C$^8$), 109.5 (C$^7$), 106.9 (C$^6$), 56.5 (CH$_3$), 55.9 (CH$_3$). HRMS: Calculated for [M+Na]+331.0728; Measured: 331.0728. IR: 3368 (v$_{as}$ NH$_2$), 3008 (v Car-H), 2834 (v OC—H), 1590 (δ NH$_2$), 1214 (v Csp$^2$-O-Csp$^3$).

Example 8:
4-amino-N-(2-methoxyphenyl)-benzenesulfonamide (18)

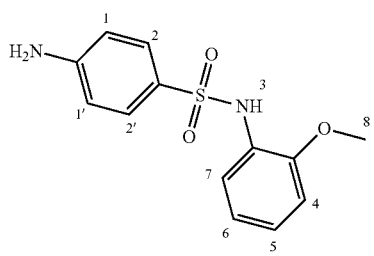

To a solution of N-(2-methoxyphenyl)-4-nitrobenzenesulfonamide (0.800 g, 2.60 mmol) in MeOH were successively added iron (0.850 g, 15.2 mmol) and an aqueous solution of NH$_4$Cl (1.380 g, 26 mmol in 20 mL of H$_2$O). After stirring over 24 hours at 65° C., the reaction mixture was filtered through a pad of celite on sintered funnel. After successive washings with acetone, DCM and ethyl acetate, the biphasic mixture was separated. The aqueous layer was extracted twice with DCM. The combined organic layers were dried over MgSO$_4$ and the solvents were concentrated under vacuum. The crude was purified by chromatography over silica gel (80/20 to 0/100) affording the expected compound (18) as a light brown solid (0.61 g, 2.2 mmol) with 84% yield. (Rf=0.26 (PE/EtOAc: 6/4); mp=193.9° C.). $^1$H NMR (300 MHz, DMSO) δ: 8.80 (s, 1H, NH), 7.35 (dd, J$_{7-5}$=1.6 Hz, J$_{7-6}$=7.8 Hz, 1H, H$_7$), 7.03 (m, 1H, H$_6$), 6.90 (dd, J$_{4-6}$=1.3 Hz, J$_{4-5}$=8.1 Hz, 1H, H$_4$), 6.82 (dt, J$_{5-6}$=1.3 Hz, J$_{5-4}$=8.1 Hz, 1H, H$_5$), 6.51 (m, 2H, H$_1$ and H$_1$), 5.92 (s, 2H, NH$_2$) 3.59 (s, 3H, H$_8$)$^{13}$C NMR (75 MHz, DMSO) δ: 152.7, 151.3 (C$^{IV}$Ar), 128.7 (C$_2$), 126.4 (C$^{IV}$Ar), 125.4 (C$_6$), 125.2 (C$^{IV}$Ar), 122.9 (C$_7$), 120.3 (C$_4$), 112.2 (C$_1$), 111.6 (C$_5$), 55.5 (C$_8$) MS (EI, m/z): [M$^{+\bullet}$]=278.0 HRMS: Calculated for [M+H]$^+$279.0798; Measured: 279.0796. IR (cm$^{-1}$): 3458 (v NH$_{ar}$), 3366 (v$_s$ NH$_{2ar}$), 3328 (v$_{as}$ NH$_{2ar}$), 1315 (v$_{as}$ SO$_2$)

Example 9:
4-amino-N-(2-methoxyphenyl)-benzenesulfonamide (25)

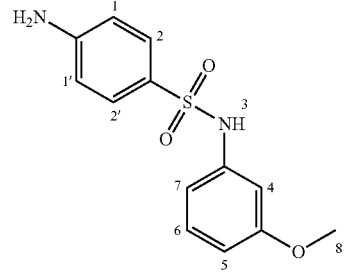 [SMILES: COc1cccc(NS(=O)(=O)c2ccc(N)cc2)c1]

To a solution of 4-amino-N-(2-methoxyphenyl)-benzenesulfonamide (1.2 g, 3.9 mmol) in MeOH were successively added iron (1.28 g, 22.8 mmol) and an aqueous solution of NH$_4$Cl (2.07 g, 39 mmol in 30 mL of H$_2$O). After stirring over 6 hours at 65° C., the reaction mixture was filtered through a pad of celite on sintered funnel. After successive washings with acetone, DCM and ethyl acetate, the biphasic mixture was separated. The aqueous layer was extracted twice with DCM. The combined organic layers were dried over MgSO$_4$ and the solvents were concentrated under vacuum. The crude was purified by chromatography over silica gel (80/20 to 0/100) affording the expected compound A427 as a light brown solid (0.73 g, 2.6 mmol) with 67% yield. (Rf=0.26 (PE/EtOAc: 6/4); mp=140.6° C.). $^1$H NMR (300 MHz, CDCl$_3$) δ 7.54 (m, 2H, H$_2$ and H$_2$), 7.49 (m, 1H, H$_7$), 7.00 (m, 1H, H$_6$), 6.95 (bs, 1H, H$_3$), 6.87 (dt, J$_{6-4}$=1.2 Hz, J$_{5-4}$=7.8 Hz, 1H, H$_5$), 6.74 (dd, J$_{4-6}$=1.2 Hz, J$_{4-5}$=7.8 Hz, 1H, H$_4$), 6.56 (m, 2H, H$_1$ and H$_1$), 3.67 (s, 3H, H$_8$)$^{13}$C NMR (100 MHz, CDCl$_3$) δ: 160.5, 150.9, 138.3 (C$^{IV}$Ar), 130.1 (C$_2$), 129.6 (C$_1$), 114.1 (C$_{ar}$), 113.7 (C$^{IV}$Ar), 113.5 (C$_{ar}$), 110.9 (C$_{ar}$), 107.1 (C$_5$), 55.5 (C$_8$) MS (EI, m/z): [M$^{+\bullet}$]=278.1 HRMS: Calculated for [M+H]$^+$ 279.0798;

Measured: 279.0796. IR (cm$^{-1}$): 3407 (v NH$_{ar}$), 3338 (v$_s$ NH$_{2ar}$), 3139 (v=C—H), 1315 (v$_{as}$ SO$_2$)

Example 10:
N-(2,4-dimethoxyphenyl)-4-aminobenzenesulfonamide

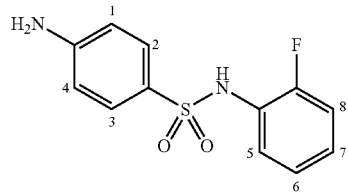

N-(2,4-dimethoxyphenyl)-4-nitrobenzenesulfonamide (11.15 mmol, 3.30 g) was dissolved in methanol (125 mL). Ammonium chloride (113 mmol, 6 g), dissolved in distillated water (67 mL), and iron (65.33 mmol, 3.65 g) were then added to the reaction mixture. After stirring overnight at 65° C., the reaction mixture was filtered through a pad of celite on sintered funnel. After successive washings with acetone, DCM and ethyl acetate, the biphasic mixture was separated. The aqueous layer was extracted twice with DCM. The combined organic layers were dried over MgSO$_4$ and the solvents were concentrated under vacuum. The crude was purified by chromatography over silica gel affording N-(2,4-dimethoxyphenyl)-4-nitrobenzenesulfonamide (7.89 mmol, 2.10 g) with 70% yield. (Rf: 0.44 (DCM 100%); mp=190° C.). RMN $^1$H (300 MHz, DMSO-d6): 8.41 (s, 1H, NH), 7.34 (d, 2H, H$^2$—H$^3$), 7.21-7.25 (m, 1H, H$^6$), 7.09-7.12 (m, 3H, H$^5$—H$^7$—H$^8$), 6.54 (d, 2H, H$^1$—H$^4$), 5.96 (s, 2H, NH$_2$). RMN $^{13}$C (75 MHz, DMSO-d6): [154.0-156.4] (C—F), 152.9 (C$^{IV}$), 128.6 (C$^2$—C$^3$), [126.3-126.4] (Car), 125.6 (C$^6$), [125.2-125.3] (C$^{IV}$), 124.7 (C$^{IV}$), [124.3-124.4] (C$^{IV}$), [115.7-115.9] (C$^8$), 112.5 (C$^1$—C$^4$). HRMS: Calculated for [M+Na]$^+$289.0423; Measured: 289.0435 IR (cm$^{-1}$): 3402 (v NH$_{ar}$), 3337 (v$_s$ NH$_{2ar}$), 1644, 1592, 1495, 1318 (v$_{as}$ SO$_2$), 1148, 1090.

Example 11: N-(4-(N-(2,4-dimethoxyphenyl)sulfamoyl)phenyl)-3-(p-tolylthio)propanamide (1)

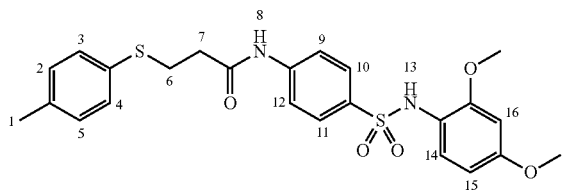

In a 50 mL flask, 3-(p-tolylthio)propanoic acid (0.5 g, 2.55 mmol) was dissolved in dry DCM (10 mL) under argon atmosphere. Oxalyl chloride (0.22 mL, 2.55 mmol) and DMF (0.03 mL) were successively added to the reaction mixture at 0° C. After 15 minutes of stirring, the apparition of bubbles stopped. Oxalyl chloride and DCM were evaporated under vacuum. To a solution of this resulting 3-(p-tolylthio)propanoyl chloride in dry DCM (15 mL) were added dropwise at 0° C. 4-amino-N-(2,4-dimethoxyphenyl) benzenesulfonamide (0.7 g, 2.55 mmol) dissolved in 2 mL of dry DCM and few crystals of DMAP. After stirring at room temperature over 48 hours, the reaction mixture was quenched with 5% sodium bicarbonate solution. The aqueous layer was extracted three times with DCM. The combined organic layers were washed successively with a molar solution of HCl, and then with brine. After drying over MgSO$_4$ and removal under vacuum of the solvent, the crude was purified by chromatography over silica gel (PE/EtOAc 7/3 to 6/4) affording the expected compound (1) as a white solid (480 mg, 0.99 mmol) with 40% yield. (Rf: 0.46 (EP/EtOAc: 1/1); mp: 153° C.). RMN $^1$H (300 MHz, CDCl$_3$): 7.59 (d, 2H, H$^{13}$—H$^{11}$), 7.49 (d, 2H, H$^9$—H$^{12}$), 7.41 (d, 1H, H$^{14}$), 7.27 (d, 2H, H$^3$—H$^4$), 7.10 (d, 2H, H$^2$—H$^5$), 6.63 (s, 1H, H$^{13}$), 6.42 (dd, 1H, H$^{15}$), 6.26 (d, 1H, H$^{16}$), 3.75 (s, 3H, CH$_3$), 3.49 (s, 3H, CH$_3$), 3.21 (t, 2H, H$^6$), 2.63 (t, 2H, H$^7$), 2.31 (s, 3H, H$^1$). RMN $^{13}$C (75 MHz, CDCl$_3$): 169.76 (CO), 158.6 (CO), 152.0 (CO), 141.7 (C$^{IV}$), 137.3 (C$^{IV}$), 134.1 (C$^{IV}$), 131.0 (C$^{IV}$), 130.9 (C$^3$—C$^4$), 130.1 (C$^2$—C$^5$), 128.7 (C$^{13}$—C$^{11}$), 124.7 (C$^{14}$), 119.0 (C$^9$—C$^{12}$), 118.6 (C$^{IV}$), 104.5 (C$^{15}$), 98.9 (C$^{16}$), 55.7 (CH$_3$), 55.6 (CH$_3$), 37.3 (C$^7$), 30.0 (C$^6$), 21.2 (C$^1$). HRMS: Calculated for [M+Na]+509.1180; Measured: 509.1175. IR: 3358 (v N—H), 3263 (v N—H), 3001 (v Car-H), 2936 (v Cal-H), 2837 (v OC—H), 1687 (v C=O), 1326 (v$_{as}$ SO$_2$), 1303 (Amide III), 1160 (v$_s$ SO$_2$).

Example 12: N-(4-(N-(2,5-dimethoxyphenyl)sulfamoyl)phenyl)-3-(p-tolylthio)propanamide (2)

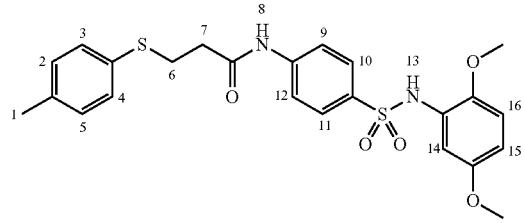

In a 50 mL flask, 3-(p-tolylthio)propanoic acid (0.38 g, 1.95 mmol) was dissolved in dry DCM (10 mL) under argon atmosphere. Oxalyl chloride (0.17 mL, 1.95 mmol) and DMF (0.03 mL) were successively added to the reaction mixture at 0° C. After 15 minutes of stirring, the apparition of bubbles stopped. Oxalyl chloride and DCM were evaporated under vacuum. To a solution of this resulting 3-(p-tolylthio)propanoyl chloride in dry DCM (10 mL) were added dropwise at 0° C. 4-amino-N-(2,5-dimethoxyphenyl) benzenesulfonamide (0.6 g, 1.95 mmol) and Et$_3$N (0.15 mL, 1.95 mmol) dissolved in dry DCM (10 mL). After stirring at room temperature over 48 hours, the reaction mixture was quenched with 5% sodium bicarbonate solution. The aqueous layer was extracted three times with DCM. The combined organic layers were washed successively with a molar solution of HCl, and then with brine. After drying over MgSO$_4$ and removal under vacuum of the solvent, the crude was purified by chromatography over silica gel (EP/AcOEt/DCM:5/2/3, then EP/AcOEt: 1/1) affording the expected compound (2) as a white solid (0.745 g, 1.53 mmol) with 78% yield. (Rf: 0.56 (EP/EtOAc: 1/1); mp: 136° C.). RMN $^1$H (300 MHz, CDCl$_3$): 7.72 (d, 2H, H$^{10}$—H$^{11}$), 7.53 (m, 2H, H$^9$—H$^{12}$—H$^{13}$), 7.29 (d, 2H, H$^9$—H$^{12}$), 7.12 (m, 4H, H$^2$—H$^5$—H$^{14}$), 6.65 (d, 1H, H$^{16}$), 6.52 (dd, 1H, H$^{15}$), 3.74 (s, 3H, CH$_3$), 3.62 (s, 3H, CH$_3$), 3.21 (t, 2H, H$^6$), 2.62 (t, 2H, H[7]), 2.31 (s, 3H, H[1]). RMN [13]C (75 MHz, CDCl$_3$): 169.6 (CO), 153.9 (CO), 143.5 (CO), 141.8 (C$^{IV}$), 137.2 (C$^{IV}$), 134.0 (C$^{IV}$), 130.9 (C$^3$—C$^4$), 130.7 (C$^{IV}$), 130.0 (C$^2$—C$^5$), 128.6 (C$^{10}$—C$^{11}$), 126.5 (C$^{IV}$), 119.0 (C$^9$—C$^{12}$), 111.5 (C$^{16}$), 109.7 (C$^{15}$), 107.0 (C$^{14}$), 56.2 (CH$_3$), 55.8 (CH$_3$), 37.2 (C$^7$), 29.9 (C$^8$), 21.0 (C$^1$). HRMS: Calculated for [M+Na]$^+$: 509.1181; Measured: 509.1181. IR: 3308 (ν N—H), 3066 (ν Car-H), 2952 (ν Cal-H), 2832 (ν OC—H), 1689 (ν C=O), 1329 (ν$_{as}$ SO$_2$), 1307 (Amide III), 1148 (ν$_s$ SO$_2$)

Example 13: N-(4-(N-(2-methoxyphenyl)sulfamoyl) phenyl)-3-(p-tolylthio) propanamide (19)

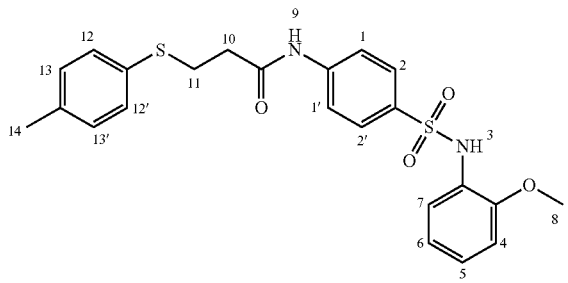

In a 50 mL flask, 3-(p-tolylthio)propanoic acid (1.68 g, 8.40 mmol) was dissolved in dry DCM (25 mL) under argon atmosphere. Oxalyl chloride (1.8 mL, 8.62 mmol) and DMF (0.03 mL) were successively added to the reaction mixture at 0° C. After 15 minutes of stirring, the apparition of bubbles stopped. Oxalyl chloride and DCM were evaporated under vacuum. To a solution of this resulting 3-(p-tolylthio) propanoyl chloride in dry DCM (10 mL) were added dropwise at 0° C. 4-amino-N-(2-methoxyphenyl)-benzenesulfonamide (0.56 g, 1.81 mmol) and Et$_3$N (0.60 mL, 8.2 mmol) dissolved in dry DCM (20 mL). After stirring at room temperature over 48 hours. After addition of n-Butylamine (1 mL), the reaction mixture was stirred at room temperature over 48 hours. The solvents were removed under vacuum and the crude was purified by recrystallization with EtOAc and PE affording the expected compound (19) as a white solid (0.261 g, 0.5 mmol) with 20% yield. (Rf=0.26 (PE/EtOAc:7/3); mp=143.5° C.). $^1$H NMR (300 MHz, CDCl$_3$) δ 7.68 (m, 2H, H$_2$ and H$_{2'}$), 7.55 (s, 1H, N—H$_3$ or N—H$_9$), 7.50 (m, 3H, H$_1$, H$_{1'}$ and H$_7$), 7.27 (m, 2H, H$_{12}$ and H$_{12'}$), 7.10 (m, 2H, H$_{13}$ and H$_{13'}$), 7.02 (dt, J$_{7-5}$=1.6 Hz, J$_{7-6}$=7.8 Hz, 1H, H$_6$), 6.98 (s, 1H, N—H$_3$ or N—H$_9$), 6.88 (dt, J$_{6-4}$=1.2 Hz, J$_{5-4}$=7.8 Hz, 1H, H$_5$), 6.73 (dd, J$_{4-6}$=1.2 Hz, J$_{4-5}$=7.8 Hz, 1H, H$_4$), 3.64 (s, 3H, H$_8$), 3.21 (t, J$_{11-10}$=6.9 Hz, 2H, H$_{11}$), 2.61 (t, J$_{10-11}$=6.9 Hz, 2H, H$_{10}$), 2.30 (s, 3H, H$_{14}$)$^{13}$C NMR (75 MHz, CDCl$_3$) δ 169.7, 149.7, 141.9, 137.4, 134.3 (C$^{IV}$ Ar), 131.0 (C$_{12}$), 131.0 (C$^{IV}$ Ar), 130.1 (C$_{13}$), 128.7 (C$_2$), 126.0 (C$_6$), 121.3 (C$_7$), 121.3 (C$_5$), 119.2 (C$_1$), 110.8 (C$_4$), 55.8 (C$_8$), 37.4 (C$_{10}$), 30.1 (C$_{11}$), 21.2 (C$_{14}$) MS (EI, m/z): [M$^{+\bullet}$]=456.1 HRMS: Calculated for [M+H]$^+$: 457.1250; Measured: 457.1250. IR (cm$^{-1}$): 3359 (ν NH$_{ar}$), 3169 (ν=C—H), 1692 (ν C=O), 1337 (ν$_{as}$ SO$_2$), 651 (ν C—S).

Example 14: N-(4-(N-(3-methoxyphenyl)sulfamoyl) phenyl)-3-(p-tolylthio) propanamide (23)

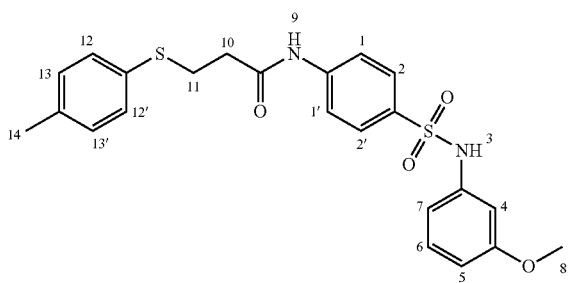

In a 50 mL flask, 3-(p-tolylthio)propanoic acid (0.84 g, 4.31 mmol) was dissolved in dry DCM (20 mL) under argon atmosphere. Oxalyl chloride (0.89 mL, 4.64 mmol) and DMF (0.03 mL) were successively added to the reaction mixture at 0° C. After 15 minutes of stirring, the apparition of bubbles stopped. Oxalyl chloride and DCM were evaporated under vacuum. To a solution of this resulting 3-(p-tolylthio)propanoyl chloride in dry DCM (20 mL) were added dropwise at 0° C. 4-amino-N-(2-methoxyphenyl)-benzenesulfonamide (0.6 g, 2.16 mmol) and Et$_3$N (0.60 mL, 8.2 mmol) dissolved in dry DCM (20 mL). After stirring at room temperature over 48 hours, the solvents were removed under vacuum and the crude was purified by chromatography over silica gel (EP/AcOEt: 1/1), and then recrystallization with EtOAc and PE affording the expected compound (23) as a white solid (0.168 g, 0.37 mmol) with 17% yield. (Rf=0.26 (PE/EtOAc: 7/3); mp=156.8° C.). $^1$H NMR (300 MHz, CDCl$_3$) δ 7.70 (m, 2H, H$_2$ and H$_{2'}$), 7.59 (s, 1H, N—H$_3$ or N—H$_9$), 7.55 (m, 2H, H$_1$ and H$_{1'}$), 7.28 (m, 2H, H$_{12}$ and H$_{12'}$), 7.11 (m, 3H, H$_{ar}$), 6.62 (m, 4H, H$_{ar}$), 3.74 (s, 3H, H$_8$), 3.22 (t, J$_{11-10}$=6.9 Hz, 2H, H$_{11}$), 2.63 (t, J$_{10-11}$=6.9 Hz, 2H, H$_{10}$), 2.31 (s, 3H, H$_{14}$)$^{13}$C NMR (75 MHz, CDCl$_3$) δ 169.8, 160.5, 142.0, 137.7 (C$^{IV}$ Ar), 134.1 (C$_{ar}$) 131.1 (C$_{12}$), 130.8, 130.3 (C$^{IV}$ Ar), 130.2 (C$_{ar}$), 128.8 (C$_2$), 119.4 (C$_1$), 113.7, 111.2, 107.4, 104.8 (Car), 55.5 (C$_8$), 37.4 (C$_{10}$), 30.1 (C$_{11}$), 21.2 (C$_{14}$) MS (EI, m/z): [M$^{+\bullet}$]=456.1 HRMS: Calculated for [M+H]$^+$: 457.1250; Measured: 457.1249. IR (cm-1): 3346 (ν NH$_{ar}$), 3180 (ν=C—H), 1680 (ν C=O), 1332 (ν$_{as}$ SO$_2$), 833 (ν C—S).

Example 15: N-(4-(N-(2-fluorophenyl)sulfamoyl) phenyl)-3-(p-tolylthio) propanamide (30)

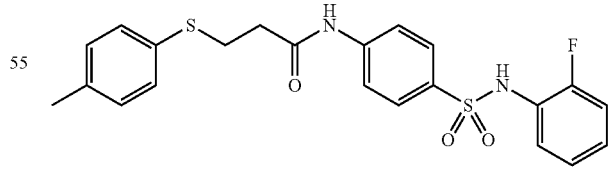

In a 25 mL flask, 3-(p-tolylthio)propanoic acid (0.222 g, 1.13 mmol) was dissolved in dry DCM (4 mL) under argon atmosphere. Oxalyl chloride (0.1 mL, 1.13 mmol) and DMF (0.03 mL) were successively added to the reaction mixture at 0° C. After 15 minutes of stirring, the apparition of bubbles stopped. Oxalyl chloride and DCM were evaporated under vacuum.

To a solution of this resulting 3-(p-tolylthio)propanoyl chloride in dry DCM (5 mL) were added dropwise at 0° C. 4-amino-N-(2-fluorophenyl)-benzenesulfonamide (0.3 g, 1.13 mmol) and Et$_3$N (0.16 mL, 1.13 mmol) dissolved in dry DCM (5 mL). After stirring at room temperature over 24 hours, the reaction mixture was quenched with 5% sodium bicarbonate solution. The aqueous layer was extracted three times with DCM. The combined organic layers were washed successively with a molar solution of HCl, and then with brine. After drying over MgSO$_4$ and removal under vacuum of the solvent, the expected compound was precipitated off from the crude with cold MeOH crude affording the expected compound (30) as a white solid (Rf: 0.12 (DCM); mp: 162° C.). RMN $^1$H (300 MHz, DMSO-d6): 10.33 (s, 1H, N$\underline{H}$), 10.03 (s, 1H, N$\underline{H}$), 7.70 (d, 2H, Har), 7.63 (d, 2H, Har), 7.11-7.28 (m, 8H, Har), 3.18 (t, 2H, H6), 2.65 (t, 2H, H7), 2.26 (s, 3H, H1). RMN $^{13}$C (75 MHz, DMSO-d6): 170.0 (CO), [157.3-154.0] (CF), 142.9 (C$^{IV}$), 135.6 (C$^{IV}$), 133.6 (C$^{IV}$), 131.8 (C$^{IV}$), 129.8 (C$^2$—C$^6$), 129.2 (C$^3$—C$^4$), 127.9 (C$^9$—C$^{16}$), [127.3-127.2] (C$^{13}$), 126.5 (C$^{IV}$), [124.7-124.6] (C$^{14}$), [124.6-124.4] (C$^{15}$), 118.6 (C$^8$—C$^{11}$), [116.1-115.9] (C$^{12}$), 36.3 (C$^7$), 28.4 (C$^6$), 20.5 (C$^1$). HRMS: Calculated for [M+H]$^+$:445.1056; Measured: 445.1045. IR: 3316 (v N—H), 3019 (v C—H), 1672 (v C=O), 1492 (v C=O), 1332 (v SO$_2$), 653 (δ C—H), 603 (γ N—H).

Example 16: N-(4-(N-(2,5-dimethoxyphenyl)sulfamoyl)phenyl)-4-(p-tolyl) butanamide (3)

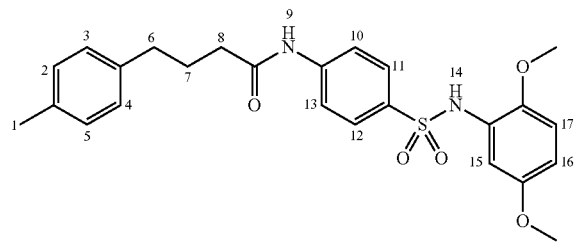

In a 25 mL flask, 3-(p-tolylthio)propanoic acid (0.95 g, 5.43 mmol) was dissolved in dry DCM (17 mL) under argon atmosphere. Oxalyl chloride (0.46 mL, 5.43 mmol) and DMF (0.03 mL) were successively added to the reaction mixture at 0° C. After 15 minutes of stirring, the apparition of bubbles stopped. Oxalyl chloride and DCM were evaporated under vacuum.

To a solution of this resulting 3-(p-tolylthio)propanoyl chloride in dry DCM (1.5 mL) were added dropwise at 0° C. 4-amino-N-(2,5-dimethoxyphenyl) benzenesulfonamide (0.56 g, 1.81 mmol) dissolved in 12 mL of dry DCM and Et$_3$N (0.36 mL, 2.7 mmol). After stirring at room temperature over 24 hours, the reaction mixture was quenched with 5% sodium bicarbonate solution. The aqueous layer was extracted three times with DCM. The combined organic layers were washed successively with a molar solution of HCl, and then with brine. After drying over MgSO$_4$ and removal under vacuum of the solvent, the crude was purified by chromatography over silica gel (PE/EtOAc: 8/2 to 1/1) affording the expected compound (3) as a white solid (0.250 g, 0.533 mmol) with 30% yield. (Rf: 0.62 (DCM/EtOAc: 9/1); mp: 126° C.). RMN $^1$H (300 MHz, CDCl$_3$): 7.70 (d, 2H, H$^{11}$—H$^{12}$), 7.68 (d, 2H, H$^{10}$—H$^{13}$), 7.45 (s, 1H, H$^{15}$), 7.13 (m, 5H, H$^{2-5}$—H$^{15}$), 6.52 (dd, 1H, H$^{16}$), 3.73 (s, 3H, CH$_3$), 3.61 (s, 3H, CH$_3$), 2.63 (t, 2H, H$^8$), 2.32 (m, 5H, H$^1$—H$^6$), 2.01 (q, 2H, H$^7$). RMN $^{13}$C (75 MHz, CDCl$_3$): 171.5 (CO), 153.8 (CO), 143.5 (CO), 142.2 (C$^{IV}$), 138.0 (C$^{IV}$), 135.6 (C$^{IV}$), 133.6 (C$^{IV}$), 129.2-128.6 (C$^{2-5}$), 128.4 (C$^{11}$—C$^{12}$), 126.5 (C$^{IV}$), 118.9 (C$^{10}$—C$^{13}$), 111.5 (C$^{17}$), 109.7 (C$^{16}$), 107.1 (C$^{15}$), 56.2 (CH$_3$), 55.8 (CH$_3$), 36.7 (C$^7$), 34.5 (C$^8$), 31.0 (C$^6$), 26.7 (C$^7$), 21.0 (C$^1$). HRMS: Calculated for [M+Na]$^+$: 491.1617; Measured: 491.1617 IR: 3316 (v N—H), 3267 (v N—H), 3025 (v Car-H), 2943 (v Cal-H), 2841 (v OC—H), 1663 (v C=O), 1338 (v$_{as}$ SO$_2$), 1312 (Amide III), 1157 (v$_s$ SO$_2$)

Example 17: N-(4-N-(2,5-dimethoxyphenyl)sulfamoyl)phenyl)-2-(p-tolylthio)acetamide (4)

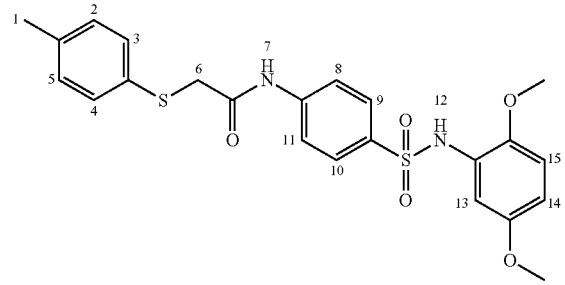

In a 50 mL flask, 3-(p-tolylthio)ethanoic acid (0.99 g, 5.43 mmol) was dissolved in dry DCM (17 mL) under argon atmosphere. Oxalyl chloride (0.46 mL, 5.43 mmol) and DMF (0.03 mL) were successively added to the reaction mixture at 0° C. After 15 minutes of stirring, the apparition of bubbles stopped. Oxalyl chloride and DCM were evaporated under vacuum.

To a solution of this resulting 3-(p-tolylthio)propanoyl chloride in dry DCM (1.5 mL) were added dropwise at 0° C. 4-amino-N-(2,5-dimethoxyphenyl)benzenesulfonamide (0.56 g, 1.81 mmol) dissolved in 12 mL of dry DCM and Et$_3$N (0.36 mL, 2.7 mmol). After stirring at room temperature over 24 hours, the reaction mixture was quenched with 5% sodium bicarbonate solution. The aqueous layer was extracted three times with DCM. The combined organic layers were washed successively with a molar solution of HCl, and then with brine. After drying over MgSO$_4$ and removal under vacuum of the solvent, the crude was purified by precipitation in hexane affording the expected compound (4) as a light brown solid (0.55 mg, 1.17 mmol) with 65% yield (Rf: 0.57 (DCM/EtOAc: 9/1); mp: 126° C.). RMN $^1$H (300 MHz, CDCl$_3$): 8.72 (s, 1H, H$^7$), 7.72 (d, 2H, H$^9$—H$^{10}$), 7.54 (d, 2H, H$^8$—H$^{11}$), 7.23 (d, 2H, H$^3$—H$^4$), 7.10 (m, 4H, H$^2$—H$^5$—H$^{12}$—H$^{13}$), 6.64 (d, 1H, H$^{15}$), 6.53 (dd, 1H, H$^{14}$), 3.74 (s, 3H, CH$_3$), 3.71 (s, 2H, H$^6$), 3.60 (s, 3H, CH$_3$). RMN $^{13}$C (75 MHz, CDCl$_3$): 166.8 (CO), 154.0 (CO), 143.6 (CO), 141.5 (C$^{IV}$), 137.9 (C$^{IV}$), 134.5 (C$^{IV}$), 130.5 (C$^3$—C$^4$), 130.0 (C$^{IV}$), 129.4 (C$^2$—C$^5$), 128.7 (C$^9$—C$^{10}$), 126.6 (C$^{IV}$), 119.2 (C$^8$—C$^{11}$), 111.6 (C$^{15}$), 109.8 (C$^{14}$), 107.1 (C$^{13}$), 56.3 (CH$_3$), 55.9 (CH$_3$), 39.4 (C$^6$), 21.2 (C$^1$). HRMS: Calculated for [M+Na]$^+$: 495.1024; Measured: 495.1024. IR: 3354 (v N—H), 3264 (v N—H), 3013 (v Car-H), 2926 (v Cal-H), 2830 (v OC—H), 1694 (v C=O), 1322 (v$_{as}$ SO$_2$), 1154 (v$_s$ SO$_2$)

Example 18: N-(4-(N-(2,5-dimethoxyphenyl)sulfamoyl)phenyl)acrylamide (5)

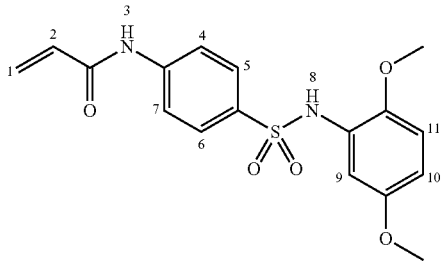

To a solution of 4-amino-N-(2,5-dimethoxyphenyl)benzenesulfonamide (0.3 g, 1.00 mmol) in dry DCM (7.5 mL) were added DIPEA (0.2 mL, 1.17 mmol) and acryloyl chloride (0.10 mL, 1.2 mmol). After stirring overnight, the reaction mixture quenched with an aqueous solution of 5% sodium bicarbonate. The aqueous layer was extracted three times with DCM. The combined organic layers were washed successively with a molar solution of HCl, and then with brine. After drying over $Na_2SO_4$ and removal under vacuum of the solvent, the crude was dissolved in dry DCM (2.5 mL). Then, n-butylamine (0.05 mL) was added and the reaction mixture was stirred at room temperature for 12 hours. After addition of hexane, the expected compound A413 was obtained by precipitation as a white solid (0.130 g, 0.36 mmol) with 36% yield. (Rf=0.31 (DCM/EtOAc: 9/1); mp: 126° C.). RMN $^1$H (300 MHz, $CDCl_3$): 7.63 (d, 4H, $H^{4-7}$), 7.03 (d, 1H, $H^9$), 6.58 (d, 1H, $H^{11}$), 6.48 (dd, 1H, $H^{10}$), 6.35 (d, 1H, $H^1$), 6.25 (dd, 1H, $H^2$), 5.69 (d, 1H, $H^1$), 3.67 (s, 3H, $CH_3$), 3.52 (s, 3H, $CH_3$). RMN $^{13}$C (75 MHz, $CDCl_3$): 164.7 (CO), 153.8 (CO), 144.1 (CO), 142.8 ($C^V$), 133.5 ($C^V$), 130.7 ($C^2$), 128.4 ($C^5$—$C^6$—$C^1$), 126.5 ($C^V$), 119.3 ($C^4$—$C^7$), 111.7 (011), 110.1 ($C^{10}$), 107.8 ($C^9$), 56.2 ($CH_3$), 55.8 ($CH_3$). HRMS: Calculated for $[M+Na]^+$: 385.0834; Measured: 385.0834. IR: 3346 (v N—H), 3001 (v Car-H), 2833 (v OC—H), 1683 (v C=O), 1332 ($v_{as}$ $SO_2$), 1284 ($\delta$ Amide III), 1156 ($v_s$ $SO_2$).

Example 19: N-(4-(N-(2,5-dimethoxyphenyl)sulfamoyl)phenyl)-3-(p-tolyloxy)propanamide (6)

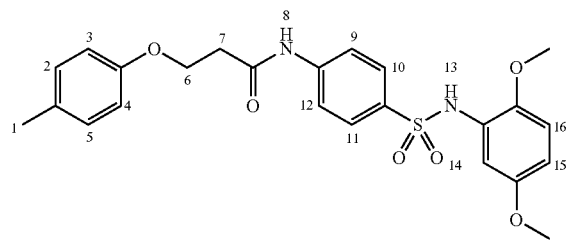

In a 50 mL flask, 3-(p-tolyloxy)propanoic acid (0.36 g, 2 mmol) was dissolved in dry DCM (6.5 mL) under argon atmosphere. Oxalyl chloride (0.17 mL, 2 mmol) and DMF (0.03 mL) were successively added to the reaction mixture at 0° C. After 15 minutes of stirring, the apparition of bubbles stopped. Oxalyl chloride and DCM were evaporated under vacuum.

To a solution of this resulting 3-(p-tolyloxy)propanoyl chloride in dry DCM (4 mL) were added dropwise at 0° C. 4-amino-N-(2,5-dimethoxyphenyl) benzenesulfonamide (0.308 g, 1 mmol) dissolved in 7 mL of dry DCM and $Et_3N$ (0.21 mL, 1.5 mmol). After 24 hours of stirring, two equivalents of acyl chloride (0.36 g, 2 mmol) were added. After additional stirring at room temperature over 24 hours, the reaction mixture was quenched with 5% sodium bicarbonate solution. The aqueous layer was extracted three times with DCM. The combined organic layers were washed successively with a molar solution of HCl, and then with brine. After drying over $MgSO_4$ and removal under vacuum of the solvent, the crude was purified by chromatography over silica gel (PE/EtOAc: 1/1) affording the expected compound (6) as a white solid (0.26 g, 0.55 mmol) with 55% yield (Rf: 0.46 (EP/EtOAc: 1/1); mp: 145° C.). RMN $^1$H (300 MHz, $CDCl_3$): 8.15 (s, 1H, $H^8$), 7.71 (d, 2H, $H^{13}$—$H^{11}$), 7.55 (d, 2H, $H^9$—$H^{12}$), 7.14 (d, 1H, $H^{14}$), 7.10 (d, 2H, $H^3$—$H^4$), 7.03 (s, 1H, $H^{13}$), 6.83 (d, 2H, $H^2$—$H^5$), 6.65 (dd, 1H, $H^{16}$), 6.52 (d, 1H, $H^{15}$), 4.28 (t, 2H, $H^6$), 3.74 (s, 3H, $CH_3$), 3.61 (s, 3H, $CH_3$), 2.82 (t, 2H, $H^7$), 2.31 (s, 3H, $H^1$). RMN $^{13}$C (75 MHz, $CDCl_3$): 169.5 (CO), 155.8 (CO), 154.1 (CO), 143.7 ($C^{IV}$), 142.1 ($C^{IV}$), 134.1 ($C^{IV}$), 131.4 ($C^{IV}$), 130.3 ($C^3$—$C^4$), 128.7 ($C^{13}$—$C^{11}$), 126.7 ($C^{IV}$), 119.3 ($C^9$—$C^{12}$), 114.7 ($C^2$—$C^5$), 111.7 ($C^{16}$), 110.0 ($C^{15}$), 107.3 ($C^{14}$), 64.3 ($C^6$), 56.4 ($CH_3$), 55.9 ($CH_3$), 37.9 ($C^7$), 20.6 ($C^1$). HRMS: Calculated for $[M+Na]^+$: 493.1409; Measured: 493.1410. IR: 3242 (v N—H), 3065 (v Car-H), 2837 (v OC—H), 1677 (v C=O), 1321 ($v_{as}$ $SO_2$), 1283 ($\delta$ Amide III), 1152 ($v_s$ $SO_2$)

Example 20: N-(2,5-dimethoxyphenyl)-4-(3-(p-tolylthio)butanamido) benzamide (8)

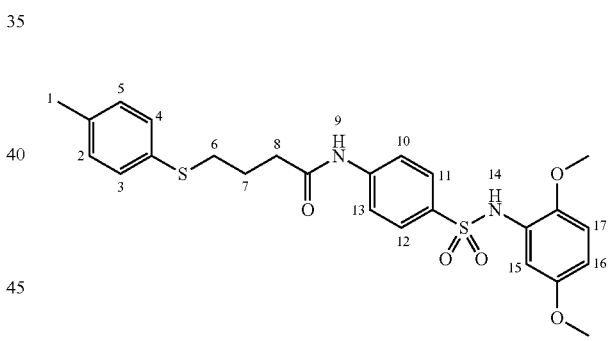

In a 25 mL flask, the 4-(p-tolylthio)butanoic acid (0.42 g, 2 mmol) was dissolved in dry DCM (2 mL) under argon atmosphere. Oxalyl chloride (0.17 mL, 2 mmol) and DMF (0.03 mL) were successively added to the reaction mixture at 0° C. After 15 minutes of stirring, the apparition of bubbles stopped. Oxalyl chloride and DCM were evaporated under vacuum.

To a solution of this resulting 4-(p-tolylthio)butanoyl chloride in dry DCM (1 mL) were added dropwise at 0° C. 4-amino-N-(2,5-dimethoxyphenyl) benzenesulfonamide (0.2 g, 0.65 mmol) dissolved in 7 mL of dry DCM and $Et_3N$ (0.11 mL, 0.78 mmol). After stirring overnight, the reaction mixture was quenched with 5% sodium bicarbonate solution. The aqueous layer was extracted three times with DCM. The combined organic layers were washed successively with a molar solution of HCl, and then with brine. After drying over $MgSO_4$ and removal under vacuum of the solvent, the crude was purified by precipitation in iPrOH affording the expected compound (8) as a white solid (0.1 g, 0.35 mmol) with 20% yield. (Rf: 0.12 (DCM); mp: 153° C.). RMN $^1$H (300 MHz, CDCl$_3$): 7.70 (d, 2H, H$^{11}$—H$^{12}$), 7.52 (d, 2H, H$^{10}$—H$^{13}$), 7.40 (s, 1H, H$^9$), 7.24 (d, 2H, H$^3$—H$^4$), 7.13 (d, 1H, H$^{15}$), 7.07 (d, 2H, H$^2$—H$^5$), 7.04 (s, 1H, H$^{14}$), 7.64 (d, 1H, H$^{17}$), 6.53 (dd, 1H, H$^{16}$), 3.74 (s, 3H, CH$_3$), 3.61 (s, 3H, CH$_3$), 2.96 (t, 2H, H$^6$), 2.51 (t, 2H, H$^8$), 2.96 (s, 3H, H$^1$), 2.01 (q, 2H, H$^7$). RMN $^{13}$C (75 MHz, CDCl$_3$): 170.9 (CO), 154.0 (CO), 143.7 (CO), 142.1 (C$^{IV}$), 136.7 (C$^{IV}$), 133.9 (C$^{IV}$), 131.9 (C$^{IV}$), 130.5 (C$^3$—C$^4$), 130.0 (C$^2$—C$^5$), 128.7 (C$^{11}$—C$^{12}$), 126.7 (C$^{IV}$), 119.1 (C$^{10}$—C$^{13}$), 111.6 (C$^{15}$), 109.9 (C$^{17}$), 107.2 (C$^{16}$), 56.4 (CH$_3$), 55.9 (CH$_3$), 35.8 (C$^8$), 33.8 (C$^6$), 24.5 (C$^7$), 21.1 (C$^1$). HRMS: Calculated for [M+Na]$^+$: 523.1337; Measured: 523.1340. IR: 3312 (v N—H), 3259 (v N—H), 2917 (v Car-H), 2832 (v OC—H), 1666 (v C=O), 1325 (v$_{as}$ SO$_2$), 1304 (Amide III), 1157 (v$_s$ SO$_2$).

Example 21: N-(4-(N-(2,5-dimethoxyphenyl)sulfamoyl)phenyl) propionamide (11)

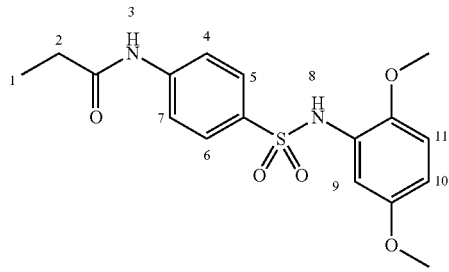 [SMILES: CCC(=O)Nc1ccc(S(=O)(=O)Nc2cc(OC)ccc2OC)cc1]

In a 25 mL flask, the propionic acid (0.36 g, 4.8 mmol) was dissolved in dry DCM (5 mL) under argon atmosphere. Oxalyl chloride (0.41 mL, 4.8 mmol) and DMF (0.03 mL) were successively added to the reaction mixture at 0° C. After 15 minutes of stirring, the apparition of bubbles stopped. Oxalyl chloride and DCM were evaporated under vacuum.

To a solution of this resulting propanoyl chloride in dry DCM (2.5 mL) were added dropwise at 0° C. 4-amino-N-(2,5-dimethoxyphenyl)benzenesulfonamide (0.5 g, 1.6 mmol) dissolved in 13 mL of dry DCM and Et$_3$N (0.67 mL, 4.8 mmol). After stirring overnight, the reaction mixture was quenched with 5% sodium bicarbonate solution. The aqueous layer was extracted three times with DCM. The combined organic layers were washed successively with a molar solution of HCl, and then with brine. After drying over Na$_2$SO$_4$ and removal under vacuum of the solvent. Part of the crude (215 mg) was then dissolved in DCM (2 mL) and n-butylamine was added (0.03 mL, 0.26 mmol). The reaction mixture was stirred overnight at room temperature. The expected compound is obtained by precipitation in hexane affording (11) as a white solid (0.150 g, 0.42 mmol) with 73% yield. (Rf: 0.05 (DCM); mp: 170° C.). RMN $^1$H (300 MHz, MeOD): 7.65 (s, 4H, H$^{4-7}$), 7.03 (d, 1H, H$^9$), 6.74 (d, 1H, H$^{11}$), 6.62 (dd, 1H, H$^{10}$), 3.72 (s, 3H, CH$_3$), 3.52 (s, 3H, CH$_3$), 2.39 (q, 2H, H$^2$), 1.18 (t, 3H, H$^1$). RMN $^{13}$C (75 MHz, MeOD): 175.6 (CO), 155.1 (CO), 147.0 (CO), 144.2 (C$^{IV}$), 135.4 (C$^{IV}$), 129.4 (C$^5$—C$^6$), 127.8 (C$^{IV}$), 120.0 (C$^4$—C$^7$), 113.0 (C$^{11}$), 111.6 (C$^{10}$), 111.3 (C$^9$), 56.6 (CH$_3$), 56.1 (CH$_3$), 31.1 (C$^2$), 9.9 (C$^1$). HRMS: Calculated for [M+Na]$^+$: 387.0991; Measured: 387.0977. IR: 3342 (v N—H), 3171 (v N—H), 2993 (v Car-H), 2925 (v Cal-H), 2834 (v OC—H), 1689 (v C=O), 1329 (v$_{as}$ SO$_2$), 1307 (Amide III), 1152 (v$_s$ SO$_2$)

Example 22: N-(4-(N-(2,5-dimethoxyphenyl)sulfamoyl)phenyl) propiolamide (27)

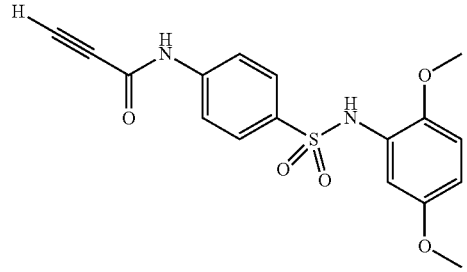 [SMILES: C#CC(=O)Nc1ccc(S(=O)(=O)Nc2cc(OC)ccc2OC)cc1]

To a solution of N-(4-(N-(2,5-dimethoxyphenyl)sulfamoyl)-3-(trimethylsilyl)propiolamide (28, 0.460 mmol, 0.200 g) in MeOH (5 mL) was added dropwise 0.7 mL of an aqueous solution of Na$_2$B$_4$O$_7$.10H$_2$O (0.070 mmol, 0.028 g). After stirring over 15 minutes at room temperature, the reaction mixture was quenched with 0.6 mL of HCl (1M). After dilution with water (10 mL), the aqueous layer was extracted three times with DCM. After drying over Na$_2$SO$_4$ and removal of the solvents under vacuum, the crude was purified by chromatography over silica gel affording the expected compound (27) as a white solid (0.25 mmol, 0.09 g) with 54% yield. (Rf: 0.09 (DCM); mp: 200° C.). RMN $^1$H (300 MHz, DMSO-d6): 11.15 (s, 1H, NH), 9.42 (s, 1H, NH), 7.70 (s, 4H, Har), 6.83 (d, 1H, H7), 6.78 (d, 1H, H9), 6.65 (dd, 1H, H8), 4.52 (s, 1H, H1), 3.64 (s, 3H, CH$_3$), 3.47 (s, 3H, CH$_3$). RMN $^{13}$C (75 MHz, DMSO-d6): 152.8 (s, CO), 150.0 (s, CO), 145.9 (s, CO), 141.7 (s, Car), 135.2 (s, Car), 128.0 (s, Car), 126.3 (s, Car), 119.3 (s, Car), 112.7 (s, C7), 110.4 (s, C9), 110.1 (s, C8), 78.1 (s, C1), 78.0 (s, C2), 56.1 (s, CH$_3$), 55.3 (s, CH$_3$). HRMS: Calculated for [M+H]$^+$: 361.0858; Measured: 361.0854. IR: 3252 (v N—H), 3230 (v N—H), 2935 (v Car-H), 2837 (v OC—H), 1652 (v C=O), 1312 (v$_{as}$ SO$_2$), 1162 (v$_s$ SO$_2$).

Example 23: N-(4-(N-(2,5-dimethoxyphenyl)sulfamoyl)phenyl)-3-(trimethylsilyl)propiolamide (28)

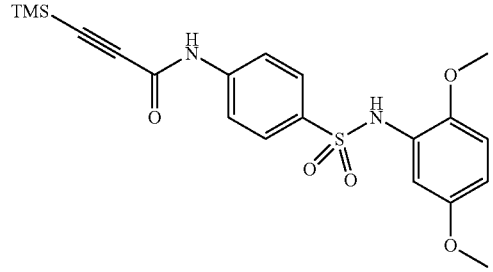 [SMILES: COc1ccc(OC)c(NS(=O)(=O)c2ccc(NC(=O)C#C[Si](C)(C)C)cc2)c1]

In a 10 mL flask, the 3-(trimethylsilyl)propiolic acid (3.24 mmol, 0.460 g) was dissolved in dry DCM (1 mL) under argon atmosphere. Oxalyl chloride (3.24 mmol, 0.27 mL) and DMF (0.03 mL) were successively added to the reaction mixture at 0° C. After 15 minutes of stirring, the apparition of bubbles stopped. Oxalyl chloride and DCM were evaporated under vacuum.

To a solution of this resulting 3-(trimethylsilyl)propynoyl chloride in dry DCM (1 mL) were added dropwise at 0° C. 4-amino-N-(2,5-dimethoxyphenyl) benzenesulfonamide (1.62 mmol, 0.500 g) dissolved in 11 mL of dry DCM and Et$_3$N (0.23 mL, 1.62 mmol). After stirring overnight, the reaction mixture was quenched with a saturated solution of NaCl. The aqueous layer was extracted three times with DCM. The combined organic layers were dried over Na$_2$SO$_4$. After removal under vacuum of the solvent, the crude was purified by chromatography over silica gel (DCM/EP: 60/40 to 100/0) affording the expected compound (28) as a white solid (0.45 g, 1.04 mmol) with 64% yield. (Rf: 0.29 (DCM); mp: 84° C.). RMN $^1$H (300 MHz, CDCl$_3$): 7.74 (d, 2H, Har), 7.58 (s, 1H, N$\underline{H}$), 7.56 (d, 2H, Har), 7.15 (d, 1H, H7), 7.01 (s, 1H, N$\underline{H}$), 6.65 (d, 1H, H5), 6.56 (dd, 1H, H6), 3.75 (s, 3H, C$\underline{H}_3$), 3.60 (s, 3H, C$\underline{H}_3$), 0.25 (s, 9H, Si—C$\underline{H}_3$). RMN $^{13}$C (75 MHz, CDCl$_3$): 154.0 (s, CO), 150.3 (s, CO), 143.7 (s, CO), 141.3 (s, Car), 134.8 (s, Car), 128.8 (s, Car), 126.5 (s, Car), 119.3 (s, Car), 111.6 (s, C5), 110.1 (s, C6), 107.4 (s, C7), 97.3 (s, Calk), 94.4 (s, Calk), 56.3 (s, $\underline{C}$H$_3$), 55.9 (s, $\underline{C}$H$_3$), −0.67 (s, Si—$\underline{C}$H$_3$). HRMS: Calculated for [M+H]$^+$: 433.1253; Measured: 433.1248. IR: 3232 (v N—H), 2956 (v Car-H), 2835 (v OC—H), 1648 (v C=O), 1313 (v$_{as}$ SO$_2$), 1152 (v$_s$ SO$_2$)

Example 24: Ethyl (4-(N-(2,5-dimethoxyphenyl) sulfamoyl)phenyl) carbamate (29)

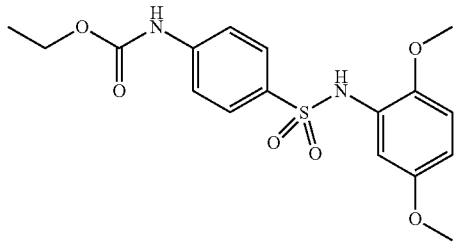 [SMILES: CCOC(=O)Nc1ccc(S(=O)(=O)Nc2cc(OC)ccc2OC)cc1]

To a solution of propiolic acid (0.65 mmol, 0.05 mL) in dry THF under argon atmosphere were added triethylamine (0.65 mmol, 0.08 mL) and then ethyl chloroformate (0.65 mmol, 0.06 mL) at room temperature under argon atmosphere. After 15 minutes of stirring at room temperature, the 4-amino-N-(2,5-dimethoxyphenyl)benzenesulfonamide (0.65 mmol, 0.200 g) was added to the reaction mixture. After stirring over 20 hours, the reaction mixture was quenched by a saturated solution of NaCl. The aqueous layer was extracted three times with DCM. The combined organic layers were dried over Na$_2$SO$_4$. After removal under vacuum of the solvent, the crude was purified by chromatography over silica gel (EP/Et$_2$O: 4/6) affording the non-desired byproduct (29) (0.10 g, 0.25 mmol) as a white solid with 38% yield. Rf: 0.25 (EP/Et$_2$O: 4/6). RMN $^1$H (300 MHz, CDCl$_3$): 7.71 (d, 2H, Har), 7.42 (d, 2H, Har), 7.14 (d, 1H, H7), 7.02 (s, 1H, N$\underline{H}$), 6.79 (s, 1H, N$\underline{H}$), 6.65 (d, 1H, H9), 6.54 (dd, 1H, H8), 4.22 (q, 2H, H2), 3.74 (s, 3H, C$\underline{H}_3$), 3.61 (s, 3H, C$\underline{H}_3$), 1.30 (t, 3H, H1). RMN $^{13}$C (75 MHz, CDCl$_3$): 154.0 (s, CO), 153.1 (s, CO), 143.7 (s, CO), 142.4 (s, Car), 133.1 (s, Car), 128.9 (s, Car), 126.8 (s, Car), 117.8 (s, Car), 111.6 (s, C9), 109.9 (s, C8), 107.2 (s, C7), 61.9 (s, C2), 56.4 ($\underline{C}$H$_3$), 55.9 ($\underline{C}$H$_3$), 14.6 (s, C1). HRMS: Calculated for [M+H]$^+$: 381.1120; Measured: 381.1113. IR: 3369 (v N—H), 2996 (v Car-H), 2960 (v Cal-H), 2836 (v OC—H), 1631 (v C=O), 1326 (v$_{as}$ SO$_2$), 1326 (v$_s$ SO$_2$)

Example 25: 2-chloro-N-(4-(N-(2,5-dimethoxyphenyl)sulfamoyl)phenyl) acetamide (31)

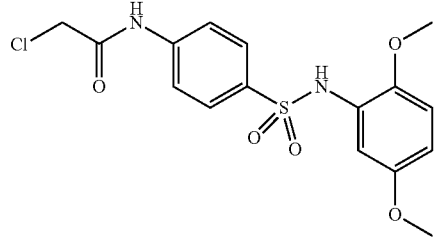 [SMILES: COc1ccc(OC)c(NS(=O)(=O)c2ccc(NC(=O)CCl)cc2)c1]

To a solution of 4-amino-N-(2,5-dimethoxyphenyl)benzenesulfonamide (0.65 mmol, 0.2 g) in DCM (1 mL) were added at 0° C. under argon atmosphere triethylamine (1.1 mmol, 0.15 mL) and 2-chloroacetyl chloride (2 mmol, 0.15 mL). After stirring 24 hours at room temperature, the reaction mixture was quenched with 5% sodium bicarbonate solution. The aqueous layer was extracted three times with DCM. The combined organic layers were washed successively with a molar solution of HCl, and then with brine. After drying over Na$_2$SO$_4$ and removal under vacuum of the solvent, the crude was purified by chromatography over silica gel (PE/DCM 2/8 to 1/9) affording the expected compound (31) (113 mg, 0.33 mmol) as a white solid with 50% yield. (Rf: 0.25 (DCM/EtOAc: 2/8); mp: 190° C.). RMN $^1$H (300 MHz, DMSO-d6): 10.64 (s, 1H, NH), 9.41 (s, 1H, NH), 7.70 (s, 4H, H$^{2-5}$), 6.83 (d, 1H, H$^8$), 6.78 (d, 1H, H$^6$), 6.65 (dd, 1H, H$^7$), 4.28 (s, 2H, H$^1$), 3.64 (s, 3H, C$\underline{H}_3$), 3.47 (s, 3H, C$\underline{H}_3$). RMN $^{13}$C (75 MHz, DMSO-d6): 165.3 (s, CO), 152.9 (s, CO), 145.9 (s, CO), 142.1 (s, C$^{IV}$), 134.8 (s, C$^{IV}$), 128.1 (s, C$^3$—C$^4$), 126.3 (s, C$^{IV}$), 118.8 (s, C$^2$—C$^5$), 112.7 (s, C$^8$), 110.5 (s, C$^6$), 110.1 (s, C$^7$), 56.1 (s, $\underline{C}$H$_3$), 55.3 (s, $\underline{C}$H$_3$), 43.6 (s, C$^1$). HRMS: Calculated for [M+H]+ 385.0625; Measured: 385.0623. IR: 3254 (v N—H), 1689 (v C=O), 1508; 1330 (v$_{as}$ SO$_2$), 1160.

Example 26: N-(2,5-dimethoxyphenyl)-4-(3-(p-tolylthio)propanamido) benzamide (7)

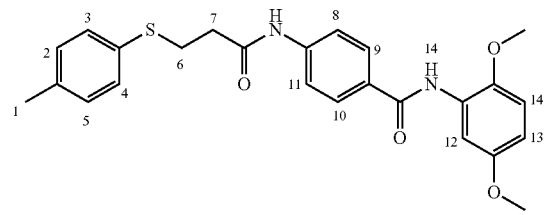

In a 25 mL flask, the 3-(p-tolylthio)propanoic acid (0.588 g, 3 mmol) was dissolved in dry DCM (9 mL) under argon atmosphere. Oxalyl chloride (0.26 mL, 3 mmol) and DMF (0.03 mL) were successively added to the reaction mixture at 0° C. After 15 minutes of stirring, the apparition of bubbles stopped. Oxalyl chloride and DCM were evaporated under vacuum.

To a solution of this resulting 3-(p-tolylthio)propanoyl-chloride in dry DCM (1 mL) were added dropwise at 0° C. 4-amino-N-(2,5-dimethoxyphenyl)benzamide (0.5 g, 1.6 mmol) dissolved in 7 mL of dry DCM and Et$_3$N (0.17 mL, 1.2 mmol). After stirring over 24 hours, the reaction mixture was quenched with 5% sodium bicarbonate solution. The aqueous layer was extracted three times with DCM. The combined organic layers were washed successively with a molar solution of HCl, and then with brine. After drying over $Na_2SO_4$ and removal under vacuum of the solvent. The crude was purified by chromatography over silica gel (DCM/EtOAc: 100/0 to 9/1) affording the expected compound (7) (0.05 g, 0.11 mmol) as a white solid with 10% yield. (Rf: 0.35 (DCM/EtOAc: 9/1); mp: 153° C.). RMN $^1$H (300 MHz, DMSO-d6): 10.25 (s, 1H, NH), 9.22 (s, 1H, NH), 7.91 (d, 2H, $H^8$—$H^{11}$), 7.71 (d, 2H, $H^9$—$H^{13}$), 7.56 (s, 1H, $H^{12}$), 7.29 (d, 2H, $H^3$—$H^4$), 7.16 (d, 2H, $H^2$—$H^6$), 7.01 (d, 1H, $H^{14}$), 6.72 (dd, 1H, $H^{13}$), 3.80 (s, 3H, $CH_3$), 3.71 (s, 3H, $CH_3$), 3.21 (t, 2H, $H^6$), 2.67 (t, 2H, $H^7$), 2.27 (s, 3H, $H^1$). RMN $^{13}$C (75 MHz, DMSO-d6): 169.7 (CO), 164.2 (CO), 152.9 (CO), 144.9 (CO), 142.2 ($C^{IV}$), 135.6 ($C^{IV}$), 131.9 ($C^{IV}$), 129.8 ($C^2$—$C^6$), 129.1 ($C^3$—$C^4$), 128.6 ($C^{IV}$), 128.4 ($C^8$—$C^{11}$), 127.8 ($C^{IV}$), 118.4 ($C^9$—$C^{13}$), 111.9 ($C^{14}$), 109.7 ($C^{12}$), 109.2 ($C^{13}$). HRMS: Calculated for [M+Na]$^+$: 473.1511; Measured 473.1510. IR: 3316 (v N—H), 3005 (v Car-H), 2912 (v Cal-H), 2838 (v OC—H), 1672 (v C=O), 1366 ($v_{as}$ $SO_2$), 1302 (δ Amide II), 1163 ($v_s$ $SO_2$)

Example 27: N-(4-(N-(2-methoxyphenyl)sulfamoyl) phenyl)-2-(p-tolylthio) acetamide (20)

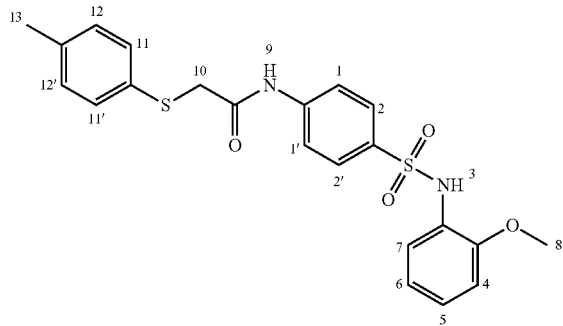

In a 50 mL flask, 3-(p-tolylthio)ethanoic acid (0.38 g, 2.01 mmol) was dissolved in dry DCM (10 mL) under argon atmosphere. Oxalyl chloride (0.4 mL, 2 mmol) and DMF (0.03 mL) were successively added to the reaction mixture at 0° C. After 15 minutes of stirring, the apparition of bubbles stopped. Oxalyl chloride and DCM were evaporated under vacuum.

To a solution of this resulting 3-(p-tolylthio)propanoyl chloride in dry DCM (3 mL) were added dropwise at 0° C. 4-amino-N-(2-methoxyphenyl)benzenesulfonamide (0.286 g, 1 mmol) dissolved in 10 mL of dry DCM and $Et_3N$ (0.3 mL, 2 mmol). After stirring at room temperature over 60 hours, the reaction mixture was quenched with 5% sodium bicarbonate solution. The aqueous layer was extracted three times with DCM. The combined organic layers were washed successively with a molar solution of HCl, and then with brine. After drying over $MgSO_4$ and removal under vacuum of the solvent, the crude was purified by chromatography over silica gel (PE/EtOAc: 7/3 then PE/EtOAc: 4/6) affording the expected compound (20) as a white solid (0.193 g, 1.17 mmol) with 43% yield. (Rf=0.23 (PE/EtOAc: 7/3); mp=169.3° C.). $^1$H NMR (300 MHz, CDCl$_3$) δ 8.70 (s, 1H, N—$H_3$ or N—$H_9$), 7.70 (m, 2H, $H_2$ and $H_{2'}$), 7.52 (m, 3H, $H_1$, $H_{1'}$ and $H_7$), 7.22 (m, 2H, $H_{11}$ and $H_{11'}$), 7.14 (m, 2H, $H_{12}$ and $H_{12'}$), 7.02 (m, 1H, $H_6$), 6.99 (s, 1H, N—$H_3$ or N—$H_9$), 6.88 (dt, $J_{6-4}$=1.2 Hz, $J_{5-4}$=7.8 Hz, 1H, $H_5$), 6.72 (dd, $J_{4-6}$=1.2 Hz, $J_{4-5}$=7.8 Hz, 1H, $H_4$), 3.7 (s, 2H, $H_{10}$), 3.64 (s, 3H, $H_8$), 2.30 (s, 3H, $H_{13}$) $^{13}$C NMR (75 MHz, CDCl$_3$) δ 166.6, 149.3, 141.2, 135.4, 134.7 ($C^{IV}$ Ar), 130.4 ($C_{12}$), 129.8 ($C^{IV}$ Ar), 129.3 ($C_{13}$), 128.6 ($C_2$), 125.4 ($C_6$) 121.1 ($C_1$), 121.0 ($O_5$), 119.0 ($C_7$), 110.6 ($C_4$), 55.8 ($C_8$), 37.4 ($C_{10}$), 30.1 ($C_{11}$), 21.2 ($C_{14}$) MS (EI, m/z): [M$^{+\bullet}$]=442.1 HRMS: Calculated for [M+H]$^+$: 443.1094; Measured 443.1093. IR (cm$^{-1}$): 3223 (v $NH_{ar}$), 3113 (v=C—H), 1679 (v C=O), 1339 ($v_{as}$ $SO_2$), 690 (v C—S).

Example 28: N-(4-(N-(2,5-di methoxyphenyl)sulfamoyl)phenyl)-3-(p-tolylsulfinyl)propanamide (24)

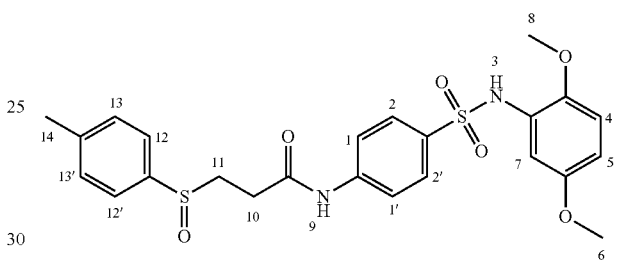

To a solution of N-(4-(N-(2,5-dimethoxyphenyl)sulfamoyl)phenyl)-3-(p-tolylthio)propanamide (2) (300 mg, 0.6 mmol) in EtOH (3 ml) and DCM (2 ml) were successively added $H_2O_2$ (30% in water) (0.06 ml, 1.2 mmol) and trifluoromethanesulfonic anhydride (0.102 ml, 0.3 mmol). After stirring over 30 minutes at room temperature, the reaction mixture was quenched by addition of water (5 ml). The aqueous layer was extracted four times with EtOAc (4×5 ml). After drying the combined organic layer with $MgSO_4$, the volatiles were evaporated under vacuum. The crude was purified by chromatography over silica gel (PE/DCM/EtOAc: 50/30/20) affording the expected compound (24) as a white solid (251 mg, 0.51 mmol) with 85% yield. (Rf=0.17 (PE/DCM/EtOAc:5/3/2); mp=148.1° C.). $^1$H NMR (300 MHz, CDCl$_3$, δ in ppm): 9.66 (s, 1H, N—$H_3$ or N—$H_9$), 7.60 (m, 2H, $H_2$ and $H_{2'}$), 7.57 (m, 2H, $H_1$ and $H_{1'}$), 7.50 (m, 2H, $H_{12}$ and $H_{12'}$), 7.33 (m, 2H, $H_{11}$ and $H_{11'}$), 7.12 (dd, $J_{7-5}$=2.9 Hz, 1H, $H_7$), 7.04 (s, 1H, N—$H_3$ or N—$H_9$), 6.63 (d, $J_{4-5}$=8.9 Hz, 1H, $H_4$), 6.51 (dd, $J_{5-7}$=2.9 Hz, $J_{5-4}$=8.9 Hz, 1H, $H_5$), 3.72 (s, 3H, $H_8$), 3.59 (s, 3H, $H_6$), 3.37 (m, 1H, $H_{11}$), 3.05 (m, 1H, $H_{11}$), 2.97 (m, 1H, $H_{12}$), 2.80 (m, 1H, $H_{12}$), 2.39 (s, 3H, $H_{14}$) $^{13}$C NMR (75 MHz, CDCl$_3$, δ in ppm): 169.07, 154.05, 143.65, 142.77, 142.49, 138.52, 133.69 ($C^{IV}$ Ar), 130.42 ($C_{11}$) 128.57 ($C_2$), 126.83 ($C^{IV}$ Ar), 124.13 ($C_{12}$), 128.75 ($C_2$), 119.09 ($C_1$), 111.68 ($C_4$), 109.84 ($C_5$), 107.17 ($C_7$), 56.38 ($C_8$), 55.90 ($C_6$), 51.40 ($C_{11}$), 30.02 ($C_{12}$), 21.52 ($C_{14}$) MS (EI, m/z): [M$^\cdot$]=502.6 HRMS: Calculated for [M+H]$^+$: 503.1305; Measured 503.1305. IR (cm$^{-1}$): 3260 (v $NH_{ar}$), 3184 (v=C—H), 1703 (v C=O), 1333 ($v_{as}$ $SO_2$), 716 (v C—S).

Example 29: N-(4-(N-(2,5-di methoxyphenyl)sulfamoyl)phenyl)-3-tosyl-propanamide (25)

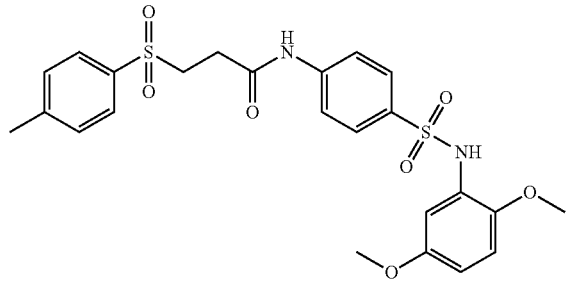

In a 50 mL flask, 3-(toluene-4-sulfonyl)propionic acid (300 mg, 1.3 mmol) was dissolved in dry DCM (10 mL) under argon atmosphere. Oxalyl chloride (1.2 mL, 1.3 mmol) and DMF (0.03 mL) were successively added to the reaction mixture at 0° C. After 15 minutes of stirring, the apparition of bubbles stopped. Oxalyl chloride and DCM were evaporated under vacuum.

To a solution of this resulting 3-(toluene-4-sulfonyl)propionyl chloride in dry DCM (10 mL) were added dropwise at 0° C. 4-amino-N-(2-methoxyphenyl)benzenesulfonamide (0.4 g, 1.3 mmol) dissolved in 10 mL of dry DCM and Et$_3$N (1 mL, 1.3 mmol). After stirring at room temperature over 48 hours, the reaction mixture was quenched with 5% sodium bicarbonate solution. The aqueous layer was extracted three times with DCM. The combined organic layers were washed successively with a molar solution of HCl, and then with brine. After drying over MgSO$_4$ and removal under vacuum of the solvent, the crude was purified by chromatography over silica gel (EP/DCM/EtOAc (5/3/2)) affording the expected compound (25) as a white solid (0.522 g; 1 mmol) with 77% yield. (Rf=0.10 (PE/DCM/EtOAc: 5/3/2); mp=180.3° C.). $^1$H NMR (400 MHz, DMSO, δ in ppm): 10.33 (s, 1H, N—H$_3$ or N—H$_9$), 7.77 (m, 2H, H$_2$ and H$_{2'}$), 7.65 (m, 2H, H$_{12}$ and H$_{12'}$), 7.58 (m, 2H, H$_{11}$ and H$_{11'}$), 7.42 (m, 2H, H$_1$ and H$_{1'}$), 6.82 (d, J$_{6-5}$=8.9 Hz, 1H, H$_6$), 6.77 (d, J$_{4-5}$=3.1 Hz, 1H, H$_4$), 6.63 (dd, J$_{4-5}$=3.1 Hz, J$_{6-5}$=1H, H$_5$), 3.63 (s, 3H, H$_7$), 3.56 (t, J$_{9-13}$=7.5 Hz, 2H, H$_9$), 3.48 (s, 3H, H$_8$), 2.68 (t, J$_{9-10}$=7.5 Hz, 2H, H$_9$), 2.34 (s, 3H, H$_{13}$) $^{13}$C NMR (75 MHz, CDCl$_3$, δ in ppm): 167.9, 152.8, 145.7 144.5, 142.4, 135.7 (C$^{IV}$ Ar), 129.8 (C$_1$) 127.8 (C$_2$), 127.8 (C$_{12}$), 118.4 (C$_{11}$), 112.7 (C$_4$), 110.1 (C$_6$), 109.8 (C$_5$), 56.1 (C$_8$), 55.2 (C$_7$), 50.6 (C$_8$), 55.90 (C$_6$), 30.7 (C$_9$), 20.9 (C$_{13}$). HRMS: Calculated for [M+]$^+$: 519.1260; Measured: 519.1263. IR (cm$^{-1}$): 3260 (ν NH$_{ar}$), 3184 (ν=C—H), 1695 (ν C=O), 1506, 1329.5 (ν$_{as}$ SO$_2$), 1147.

Example 30: N-(4-(N-(2,5-dimethoxyphenyl)-N-methylsulfamoyl)phenyl)-3-(p-tolylthio)propanamide (26)

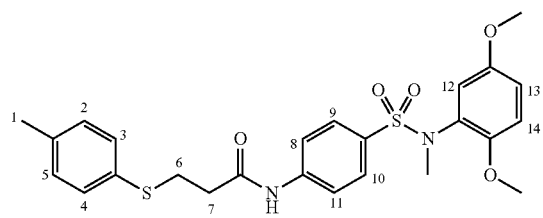

In a 25 mL flask, the 3-(p-tolylthio)propanoic acid (0.55 g, 2.82 mmol) was dissolved in dry DCM (1 mL) under argon atmosphere. Oxalyl chloride (0.24 mL, 2.82 mmol) and DMF (0.03 mL) were successively added to the reaction mixture at 0° C. After 15 minutes of stirring, the apparition of bubbles stopped. Oxalyl chloride and DCM were evaporated under vacuum.

To a solution of this resulting 3-(p-tolylthio)propanoyl-chloride in dry DCM (1 mL) were added dropwise at 0° C. 4-amino-N-(2,5-dimethoxyphenyl)-N'-Methyl-benzenesulfonamide (0.7 g, 2.17 mmol) dissolved in 14 mL of dry DCM and Et$_3$N (0.3 mL, 2.17 mmol). After stirring over 24 hours, the reaction mixture was quenched with brine. The aqueous layer was extracted three times with DCM. The combined organic layers were dried over Na$_2$SO$_4$ and the volatiles were removed under vacuum. The crude was purified by chromatography over silica gel (EP/DCM: 20/80 to 10/90) affording the expected compound (26) (45 mg) as a white solid with 5% yield (Rf: 0.12 (DCM); mp: 48° C.). RMN $^1$H (300 MHz, DMSO-d6): 10.35 (s, 4H, NH), 7.75 (d, 2H, H$^8$—H$^{11}$), 7.58 (d, 2H, H$^9$—H$^{10}$), 7.28 (d, 2H, H$^3$—H$^4$), 7.16 (d, 2H, H$^2$—H$^5$), 6.93 (d, 1H, H$^{14}$), 6.89 (dd, 1H, H$^{13}$), 6.63 (d, 1H, H$^{12}$), 3.66 (CH$_3$), 3.40 (CH$_3$), 3.20 (t, 2H, H$^6$), 3.07 (s, 3H, CH$_3$), 2.67 (t, 2H, H$^7$), 2.27 (s, 3H, H$^1$). RMN $^{13}$C (75 MHz, DMSO-d6): 169.9 (CO), 152.6 (CO), 150.4 (CO), 142.8 (C$^{IV}$), 135.6 (C$^{IV}$), 132.6 (C$^{IV}$), 131.8 (C$^{IV}$), 129.8 (C$^2$—C$^5$), 129.3 (C$^{IV}$), 129.2 (C$^3$—C$^4$), 128.4 (C$^9$—C$^{10}$), 118.5 (C$^8$—C$^{11}$), 116.4 (C$^{12}$), 114.2 (C$^{13}$), 113.2 (C$^{14}$), 55.6 (CH$_3$), 55.5 (CH$_3$), 37.8 (CH$_3$), 36.3 (C$^7$), 28.4 (C$^6$), 20.5 (C$^1$). HRMS: Calculated for [M+]$^+$:501.1518; Measured 501.1518. IR: 3332 (ν N—H), 2933 (ν Cal-H), 2835 (ν OC—H), 1695 (ν C=O), 1332 (ν$_{as}$ SO$_2$), 1308 (Amide III), 1147 (ν$_s$ SO$_2$)

Example 31: N-acryloyl-N'-(4-(N-(2,5-dimethoxyphenyl)sulfamoyl)phenyl) acrylamide (16)

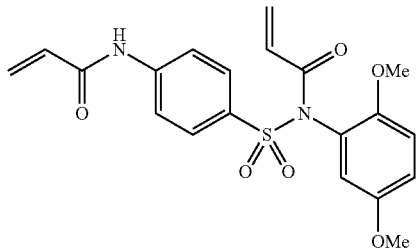 [SMILES: C=CC(=O)Nc1ccc(S(=O)(=O)N(C(=O)C=C)c2cc(OC)ccc2OC)cc1]

To a solution of 4-amino-N-(2,5-dimethoxyphenyl)benzenesulfonamide (0.6 g, 2.00 mmol) in DCM (15 ml) was added successively freshly distilled acryloyl chloride (0.5 mL, 6 mmol) and Et$_3$N (0.84 mL, 6 mmol). After TLC monitoring, the reaction showed full conversion after 48 h of stirring at room temperature. Then, the reaction mixture was quenched by a saturated solution of sodium bicarbonate. After extracting the aqueous layer three times with DCM, the combined organic layers were dried with Na$_2$SO$_4$. After filtration and concentration under vacuum, the crude mixture is obtained as a yellowish oil (0.95 g). The crude was purified by silica gel chromatography using DCM/MeOH as eluent. The expected compound (16) was obtained a white solid (0.810 g, 1.94 mmol) with 97% yield. (Rf: 0.36 (DCM/MeOH: 98/2); mp: 220.8° C.)$^1$H NMR (400 MHz, DMSO, δ in ppm): 10.66 (s, 1H, NH), 8.00 (m, 4H, H$_{arom}$), 7.1 (m, 2H, H$_{arom}$), 7.58 (m, 2H, H$_{11}$ and H$_{11'}$), 7.00 (d, 1H, $J_{4-5}$=2.7 Hz, $H_{arom}$), 6.53 (dd, 1H, J=17.0 Hz, 10.0 Hz, $H_{CH=CH2}$), 6.38 (dd, 1H, J=17.0 Hz, 1.9 Hz, $H_{CH=CH2}$), 6.25 (dd, 1H, J=17.0 Hz, 1.7 Hz, $H_{CH=CH2}$), 5.87 (m, 2H, $H_{CH=CH2}$), 5.74 (dd, 1H, J=10.3 Hz, 1.7 Hz, $H_{CH=CH2}$), 3.82 (s, 3H, OMe), 3.71 (s, 3H, OMe). $^{13}$C NMR (100.6 MHz, DMSO, Sin ppm): 164.2; 163.7; 153.1; 150.3; 143.9; 132.6; 131.5; 131.4; 130.4; 128.2; 127.8; 124.0; 118.5; 117.3; 116.7; 113.4; 56.0; 55.7. HRMS: Calculated for [M+]$^+$: 417.1120; Measured: 417.1123. IR (cm$^{-1}$): 3337 (v N—H), 2920 (v Cal-H), 1696, 1664, 1614, 1507, 1403, 1355, 1160.

Activity Results

| Chemical structure | Name | Relative activity (NSC23766) | $IC_{50}$ |
|---|---|---|---|
| | NSC23766 | — | $10\text{-}50 \cdot 10^{-6}$ M |
| (1) | | > | $3 \cdot 10^{-8}$ M |
| (2) | | > | $10^{-9}$ M |
| (5) | | > | $10^{-10}$ M |
| (6) | | > | $10^{-9}$ M |
| (17) | | > | $10^{-9}$ M |
| (18) | | > | $10^{-9}$ M |

-continued

| Chemical structure | Name | Relative activity (NSC23766) | $IC_{50}$ |
|---|---|---|---|
| | NSC23766 | — | $10\text{-}50.10^{-6}M$ |
| [structure: 4-methylphenyl-S-CH2CH2-C(O)-NH-phenyl-SO2-NH-(2-methoxyphenyl)] | (19) | > | $10^{-9}M$ |
| [structure: 4-methylphenyl-S-CH2-C(O)-NH-phenyl-SO2-NH-(2-methoxyphenyl)] | (20) | > | $10^{-9}M$ |
| [structure: H2N-phenyl-SO2-NH-(3-methoxyphenyl)] | (22) | > | $10^{-9}M$ |

FIGURES

FIG. 1 relates to the inhibition of Rac activation by A4.1 (or compound (2)). It represents immunoblot analysis of Rac-GTP and Rac total expression in fibroblasts stimulated by a Rac activator and pre-incubated or not with NSC23766 or (2) for 1 h.

Figure 2:
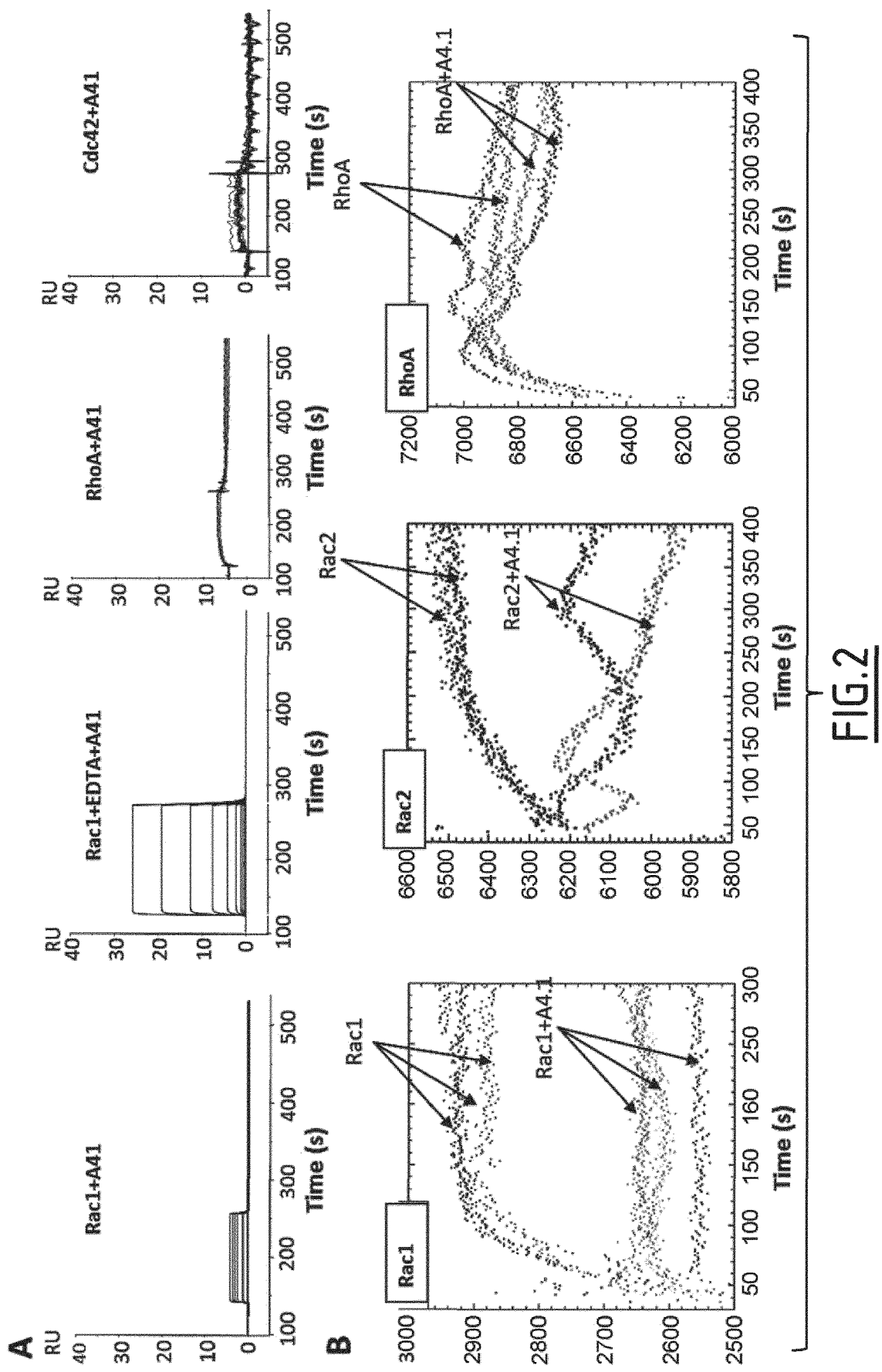

FIG. 2 relates to the analysis of A4.1 selectivity. FIG. 2A: Representative surface plasmon resonance (SPR) sensograms. (2) was injected at 0.78, 1.56, 3.1, 6.25, 12.5 and 25 µM into sensor chip coated by indicated purified small GTPase. When indicated, EDTA was added in the running buffer. n>3. FIG. 2B: Representative real-time kinetics of nucleotide exchange assay of indicated small GTases. The increase of mant-GTP or the decrease of man-GDP was recorded in presence or absence of (2) (10 µM). n=3.

Figure 3:
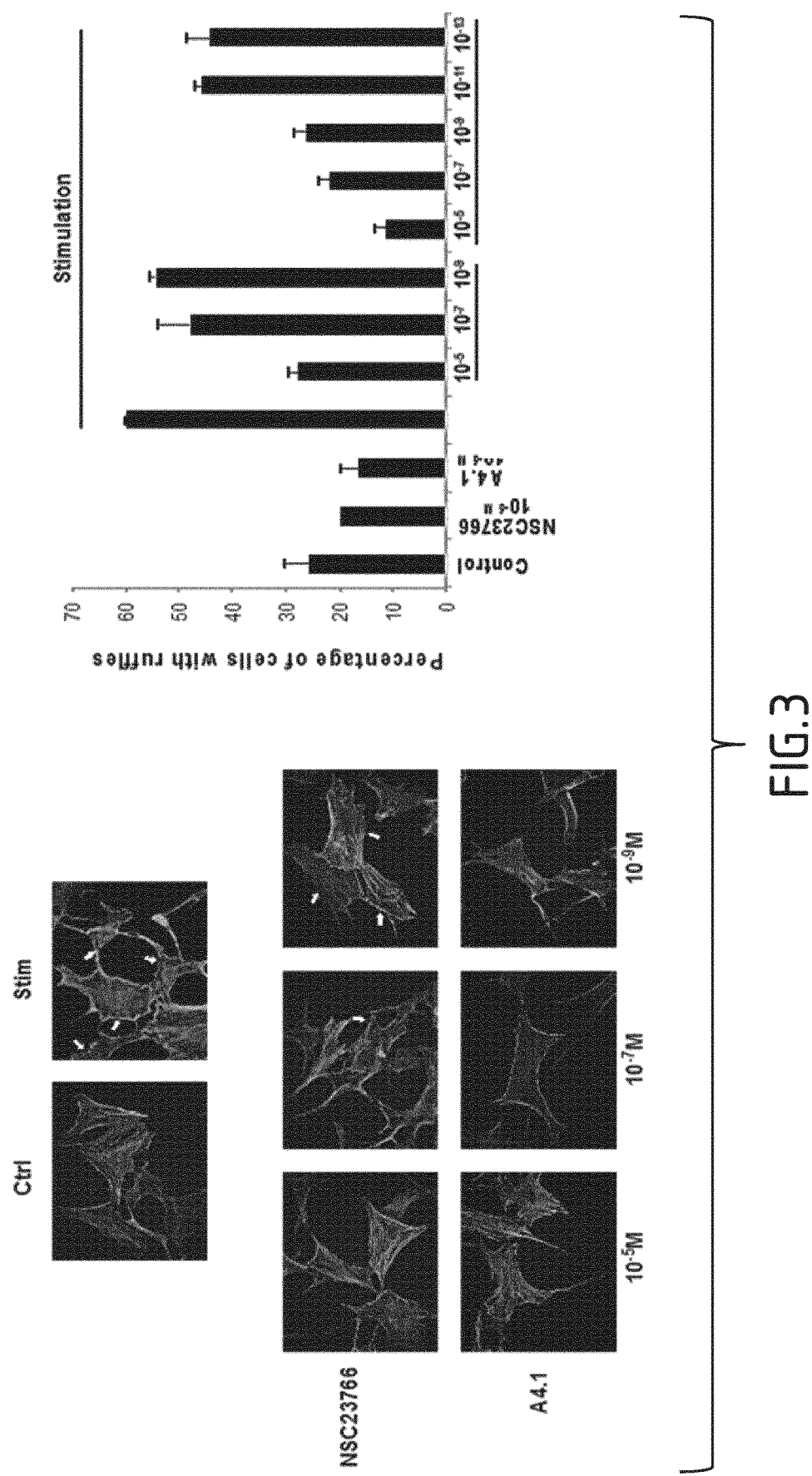
Figure 4:
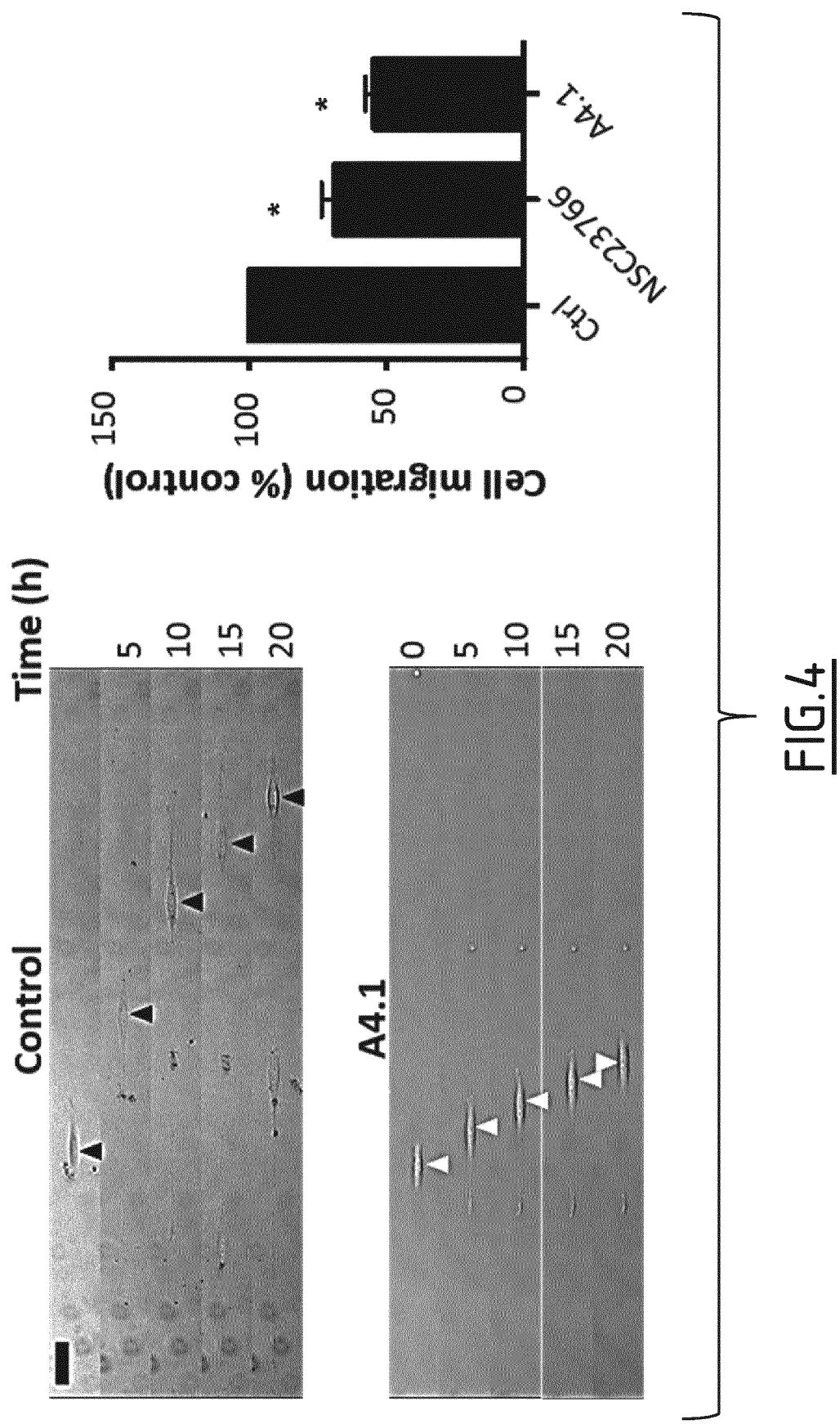
Figure 5:
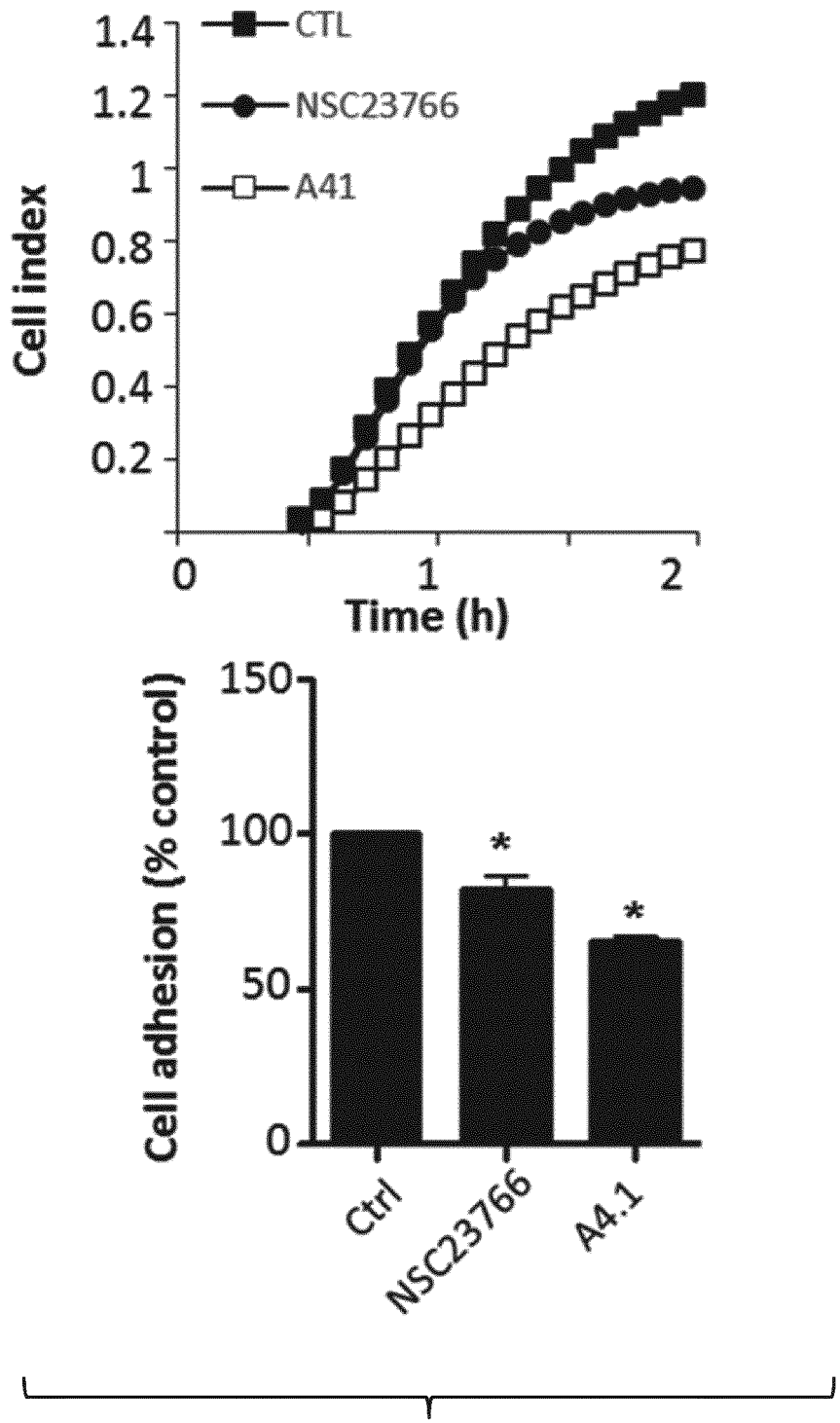

FIGS. 3 to 5 relate to the inhibition of the Rac-induced cell functions by (2). FIG. 3: (2) blocks Rac activator-induced actin reorganization. 3T3 cells were incubated in serum-free growth medium, either alone, or supplemented with (2) or NSC23766 at indicated concentration 1 h before Rac activation. Ruffles are indicated by arrows (left panel). Percentages of cells with ruffles were quantified (right panel). Results shown are representative of 3 independent experiments. FIG. 4: (2) decreases cell migration. 3T3 cells were incubated or not with (2) or NSC23766. Left panel, representative records with arrows indicating the cell location at different times. Right panel, quantification of cell speed in each experimental conditions. Results shown are representative of 2 independent experiments. FIG. 5: (2) decreases cell adhesion. Upper panel, representative kinetics of fibroblast adhesion pre-treated or not with 10 µm (2) or NSC23766. Lower panel, quantification of cell adhesion. Results shown are representative of 3 independent experiments.

Figure 6:
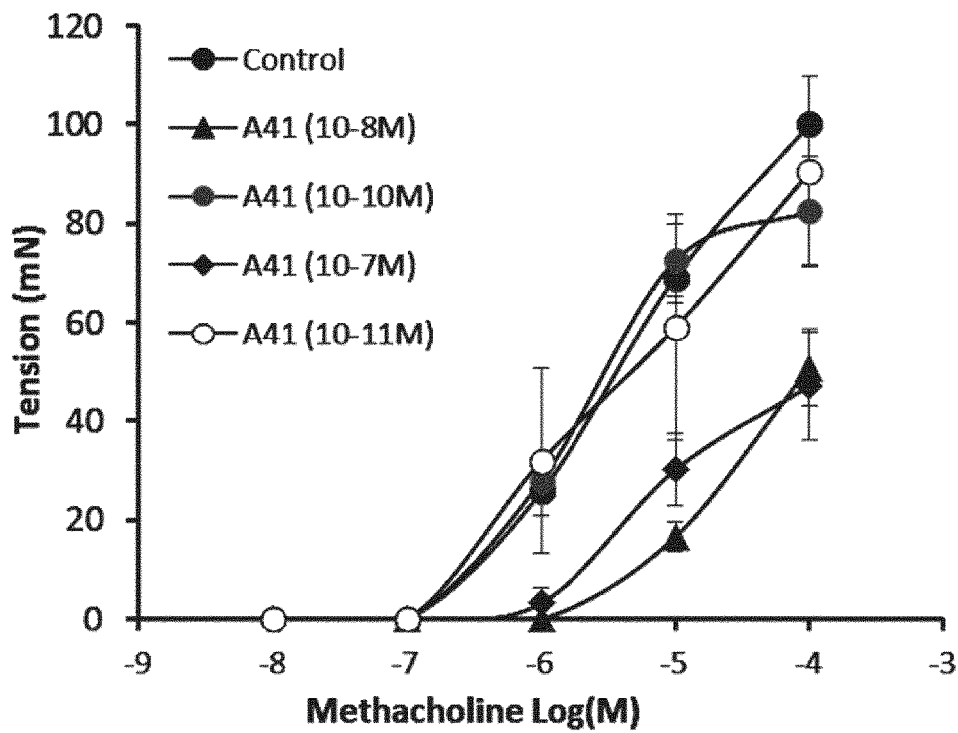
Figure 6:
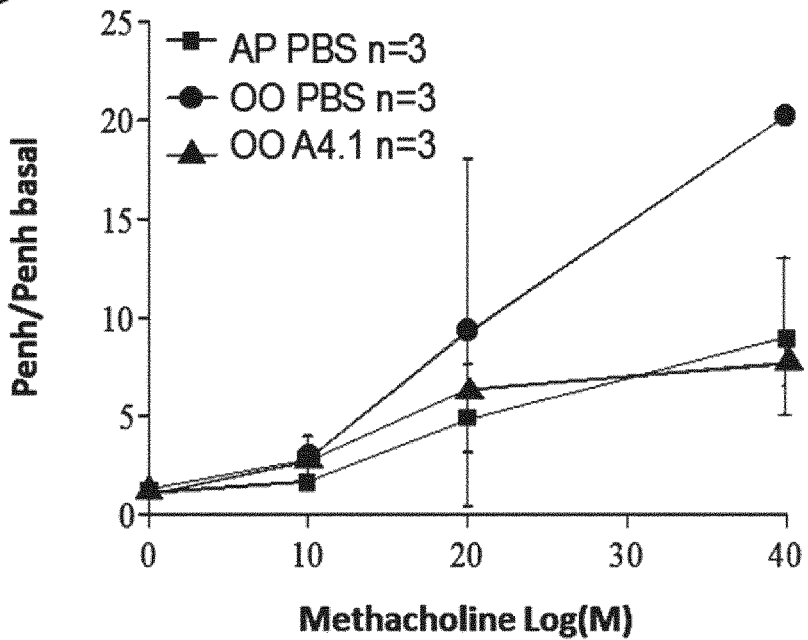

FIG. 6 relates to the inhibition of aSMC contraction by (2). FIG. 6A: Contractile responses to methacholine in bronchi from control mice. When indicated, murine bronchial rings were pre-treated with (2) before methacholine stimulation (n=5-7). FIG. 6B: Analysis of airway reactivity to methacholine challenges by non-invasive (plethysmography) in naive (AP) and ovalbumin-challenged mice (00) treated with (2) or vehicle (PBS) nebulization (n=3).

BIOLOGY RESULTS

Materials and Methods

In silico screening. The structure of Rac1 in complex with GDP was first extracted from the crystal structure of Rac1-GDP complexed with arfaptin (PDB code 114D; Tarricone et al, Nature 2001). Pharmacophore models were created from the binding site of GDP with Rac1 using the Receptor-Ligand Pharmacophore Generation tools within Accelrys Discovery Studio 4.0 (DS4.0) software package.

The pharmacophore model was used as a search query against three dimensional multi-conformational molecular databases. The HitFinder™ collection (14,400 compounds) from Maybridge (www.maybridge.com) and the DIVERSet™-EXP (50,000 compounds) and the DIVERSet™-CL (50,000 compounds) from Chembridge (www.chembridge.com) were used in the virtual screening. For the preparation of ligands, duplicate structures were removed and 3D coordinates were generated. A multi-conformational ligand database was then created using Catalyst within the Build 3D Database tool under DS4.0. The query was performed using the Search 3D Database tool with the FAST search method under DS4.0, retrieving as hits only compounds matching all features of the query.

The docking studies were performed using LigandFit option of receptor-ligand interactions protocol section available in DS4.0. Initially, Rac1 protein was prepared, by adding the hydrogen atoms and removing the water molecules, and then minimized using CHARMm force field. The protein molecule thus prepared was then defined as the total receptor, after removing GDP. The ligand molecules retained by the pharmacophore model were docked into the binding site of the Rac1 and the interaction energies in the form of dock score (Venkatachalam et al, J Mol Graph Model. 2003) between each ligand and the protein were calculated. Docking was performed using CFF as the energy grid. Penality of 200 kcal/mol/atom was set up to reduce the dock score of poses that occurred outside of the binding site. The conformational search of the ligand poses was performed by the Monte Carlo trial method. Maximum internal energy was set at 10000 kcal/mol. A short rigid body minimization was then performed (steepest descent and Broyden Fletcher Goldfarb Shanno (BFGS) minimizations). Ten poses were saved for each ligand after docking and 100 steps of BFGS rigid body minimization were then carried out. Scoring was performed with six scoring functions: LigScore1, Ligscore2 (Krammer et al, J Mol Graph Model. 2005), PLP1, PLP2 (Gehlhaar et al, Chem Biot 1995), PMF (Venkatachalam et al, J Mol Graph Model. 2003; Muegge and Martin, J Med Chem 1999) and Jain (Jain, j Comput-Aided Mol Design 1996). CFF force field was used for LigScore calculations. Best scored compounds were retained based on the calculation of a consensus score and binding energies under DS4.0.

Cell culture, transfection and actin staining. NIH3T3 cells grew up in DMEM (Gibco; Invitrogen) containing 10% foetal bovine serum, 100 units/mL penicillin and 100 μg/mL streptomycin at 37° C. and 5% $CO_2$. The culture medium was changed every 72 hours.

After treatments, fibroblasts were fixed with 4% paraformaldehyde in PBS, permeabilized in PBS 0.5% Triton X-100, and incubated with 130 μg/mL of FITC-conjugated phalloidin (Sigma) to visualize F-actin. After staining, images were captured by a fluorescence microscope (Nikon). The actin cytoskeleton organization was analyzed to observe Rac1-dependent ruffle formation.

Analysis of Rac1 activity. In NIH3T3 cells lysates, Rac1 activity was evaluated by active Rac immunoprecipitation using anti-Rac-GTP antibody (26903, NewEast Biosciences). The precipitated active Rac was subjected to SDS-PAGE and detected by immunoblot with anti-Rac1 antibody (BD biosciences).

Surface plasmon resonance studies. SPR immobilization was performed at 25° C. Rac1, RhoA and Cdc42 purified proteins were diluted to 5 μg/mL in $Na^+$ acetate buffer (pH 5.0) and injected into sensor chip CM5 (GE Healthcare) in a Biacore T200 (GE Healthcare) that was activated with NHS/EDC buffer. Approximately 5,000 response units of the purified protein were captured on the biosensor chip. Biosensor chips were blocked by an injection of 1 mM ethanolamine (pH 8.5). The Rac1 biosensor chip was validated by the injection of a dose-response curve of NSC23766 at the start of each experiment. SPR analysis was performed at 25° C. in HBSEP running buffer (5% DMSO). When indicated, EDTA (20 mM) was added in running buffer.

Unidirectional cell migration. Cells (1000/well) were seeded in a 96 well plate with 10 mm fibronectin stripes (CytooPlates Motility, CYTOO) in medium with 1% SVF and allowed to spread for 4 hours before capturing time-lapse images for 24 hours (image/10 minutes) on a Widefield Leica DMI 6000B drove with Metamorph software. Cells speed was measured with ImageJ software.

Cell adhesion assay using impedance technology. Cells (10000/well) were seeded in a 96 well plate microtiter xCELLigence assay plate (E-Plate) (ACEA Biosciences Inc.) and placed on the Real-time xCELLigence Cell Analyzer (Roche Applied Science) platform at 37° C. to measure the "cell index" every 5 min for a period of 6 hours. The cell index unit is defined as $(R_n - R_b)/15$. $R_n$ is the cell electrode impedance of the well when it contains cells. $R_b$ is the background impedance of the well with the media alone.

Nucleotide exchange assays. Full-length human small GTPases carrying a 6-histidine tag fused to their C-terminus were expressed in E. coli and purified to homogeneity. Small GTPases were loaded with GDP or N-methylanthraniloyl-GDP (GDP/mant-GDP, JenaBiosciences) before nucleotide exchange kinetics experiments.

Nucleotide exchange kinetics were monitored by fluorescence of the mant fluorophore ($\lambda exc=360$ nm, $\lambda em=440$ nm) or tryptophan fluorescence (for Arf6; $\lambda exc=280$ nm, $\lambda em=292$ nm) using a Cary Eclipse fluorimeter (Varian, Toulouse, France) at 30° C. under stirring. All kinetics assays were carried out in a buffer containing 50 mM Tris at pH 8, 300 mM NaCl, 2 mM $MgCl_2$, 1 mM DTT and were started by addition of 100 μM N-methylanthraniloy-GTP or GTP (mant-GTP/GTP, JenaBiosciences). Nucleotide exchange kinetics were carried out at a concentration of small GTPases of 1 μM, either without GEF for spontaneous exchange, in the presence of 50 nM GEF for single kobs (s-1) determination. The kobs was determined from single-exponential fit of the fluorescence change. All experiments were carried out at least in triplicate.

Airways reactivity ex vivo. Murine primary bronchi were cleaned, cut in rings and mounted on a multichannel isometric myograph in Krebs-Henseleit physiological solution (118.4 mM NaCl, 4.7 mM KCl, 2 mM $CaCl_2$, 1.2 mM $MgSO_4$, 1.2 mM $KH_2PO_4$, 25 mM $NaHCO_3$ and 11 mM glucose) at 37° C. under oxygen. A pre-tension of 0.5 mN was applied. We constructed dose-response curves to methacholine (Sigma). When indicated, rings were pre-incubated 1 h before contraction with (2) (or compound A4.1). The wire myograph was connected to a digital data recorder (MacLab/4e, AD Instruments) and recordings were analyzed using LabChart v7 software (AD Instruments).

Animals use and airways responsiveness measurement in vivo. All experimental procedures and animal care were performed in accordance with the European Community Standards on the Care and Use of Laboratory Animals and approved by the local ethics committee (Comité d'Ethique en Expérimentation Animale des Pays de Loire).

Airway responsiveness was assessed in conscious, unrestrained mice using a barometric, whole-body plethysmography (EMKA Technologies) by recording respiratory pressure curves in response to inhaled methacholine (Sigma) at concentrations of 0-40 mg/ml for 1 min. Airway responsiveness was expressed in enhanced pause (Penh) units. The Penh values measured after stimulation were averaged and expressed as the fold-increase over baseline values. When required, the Rac inhibitor (2) was nebulised (300 μl at 5 mM) 10 min before methacholine challenge.

Statistics. All data are expressed as the mean±SEM of sample size n. For multiple comparisons, the non-parametric Kruskal-Wallis test was used followed by Dunns' post-test. For individual comparisons, statistical analysis was performed using non-parametric t-test (Mann-Whitney). Data analysis was performed using the GraphPad Prism software. The threshold for statistical significance was set at P<0.05.

Results

Pharmacophore Modeling and Virtual Screening

The pharmacophore model was built using HBA (hydrogen bond acceptor) and Ring_A (ring aromatic) features. These features were created based on the observation of Rac1/GDP interactions. One HBA was centered on the oxygen atom of the guanine group of GDP and was oriented toward the N atom of residue Ala159 of Rac1. The other HBA feature was centered on the saturated oxygen of the ended phosphate group of the GDP and was oriented toward the centroid of the N atom of residues Gly12, Ala13, Val14, Gly15 and Lys16, and the NZ atom of Lys16 of Rac1. A Ring_A feature was added, centered on the imidazole group of GDP and oriented toward the aromatic group of residue Phe28 of Rac1. Location constraints were defined by spheres with radius of 1.6 and 2.2 Å on the head and tail of the latest features, respectively. Sixteen exclusion spheres were generated automatically, using the Receptor-Ligand Pharmacophore Generation tool of DS4.0. Finally, the pharmacophore model containing all the features described above, was used to search a database of 116,000 chemical compounds using the Search 3D Database tool within DS4.0. The Fit Value threshold was fixed to 1.6 and allowed to extract 9362 compounds for the docking process.

To further reduce the number of compounds to be evaluated in vitro, molecular docking studies were conducted using LigandFit module of Receptor-Ligand Interactions section available under DS4.0. Ligands molecules retained by the pharmacophore-based approach were docked into a binding site defined as the volume filled by GDP in the Rac1/GDP complex. The volume of the binding site was 606 Å3 and contained 4851 points. Among the 9362 compounds retained after the Pharmacophore-based search, 9189 were actually docked to the target. To improve the screening accuracy, a consensus strategy was adopted. The top 20% of the docked database, ranked by at least five of the six scoring functions used, were retained and for compounds with a dock score above 70, binding free energies were calculated after in situ ligand minimization. The ligands were then ranked based on the lowest binding free energy after the withdrawal of the compound poses having a high ligand free energy (threshold 20 kcal/mol). The top 100 were retained to be purchased and evaluated in vitro on Rac-dependent cellular functions: cell adhesion and migration. Thus, the hit (2) was identified as the best potential Rac inhibitor.

Compound (2) is a Potent and Selective Inhibitor of Rac Proteins

The potential of (2) to inhibit Rac activity was first evaluated by pull-down assay. As expected, the level of Rac-GTP is increased in culture cells stimulated by a Rac activator. This activation is prevented by the Rac inhibitor NSC23766 and also by (2) (FIG. 1). These results suggest that the compound (2) is a new Rac inhibitor. To further delineate the selectivity of (2), its interaction with Rho family proteins was examined by surface plasmon resonance (SPR). The SPR sensograms reveal that (2) binds Rac1 but not RhoA or Cdc42 (FIG. 2A), suggesting a selective interaction of (2) for Rac proteins. EDTA chelates $Mg^{2+}$ ions and promotes nucleotide release from Rho small GTPases. The interaction Rac1: (2) is significantly increased in Rac1 nucleotide free (FIG. 2A), strengthening the hypothesis that (2) binds Rac1 and docks into the GDP/GTP pocket To proceed with the analysis of (2) selectivity, a screening was conducted with purified proteins representing members of the Rho, Rab and Arf small GTPases subfamilies. The effect of (2) on the small GTPase ability to exchange nucleotide was analyzed by a real-time assay of mant-GTP or mant-GDP binding kinetics. The presence of the small molecule inhibitor (2) decreased the $B_{max}$ GTP-binding on Rac1 and Rac2. In contrast, (2) did not alter nucleotide exchange kinetics of RhoA, RhoG, Rab35 and Arf6 (FIG. 2B and data not shown). These results suggest that the compound (2) is a selective inhibitor of the small GTPase Rac but without specificity for Rac isoforms.

Compound (2) Inhibits Rac-Dependent Cell Functions

The small GTPase Rac is extensively described to play a crucial role in actin cytoskeleton organization, cell adhesion and migration. To evaluate the ability of (2) to inhibit Rac-mediated cell functions, the actin structures of the cells stimulated by Rac activator was examined in the presence or absence of (2). Rac activator stimulated membrane ruffling in fibroblastes (FIG. 3A). However, in the presence of (2) or NSC23766, the efficiency of Rac activator to induce ruffle is strongly decreased. Interestingly, the dose-dependent inhibition observed in fibroblastes suggest that the small molecule (2) ($IC_{50}$=0.67 nM) is a powerful Rac inhibitor compared to NSC23766 ($IC_{50}$=2.6 µM). This hypothesis is reinforced by the cell migration (FIG. 3B) and adhesion (FIG. 3C) assays. Indeed, NSC23766 and (2) slow down the migration and adhesion rate of the cells but a higher inhibition is always recorded with cells treated with the compound (2).

These in vitro assays demonstrate that (2) inhibits Rac-dependent cell functions with a higher efficiency than NSC23766.

Compound (2) Prevents Bronchoconstriction and Airway Hyperresponsiveness

Excessive contraction of airways smooth muscle cells (aSMC) is one of the main characteristics of asthma. The degree of this airway hyperresponsiveness (AHR) correlates with asthma severity and the need for therapy. However, the molecular mechanisms leading to AHR are not completely understood. Recently, we unveiled an unexpected and essential role of Rac1 in the regulation of intracellular $Ca^{2+}$ and contraction of aSMC, and the development of AHR. Rac1 thus appears as an attractive therapeutic target in asthma, with a combined beneficial action on both bronchoconstriction and pulmonary inflammation. First, the functional impact of (2) in aSMC was studied by measuring the contractile response of bronchial rings from control mice. The maximal contraction induced by the muscarinic receptor agonist methacholine was dose-dependent reduced by (2), suggesting that this small molecule could be used to induce bronchodilation (FIG. 4A). To confirm in vivo the potential therapeutic of (2), the pulmonary resistance was measured in a mouse model of human allergic asthma, induced by percutaneous sensitization and intranasal challenge with house dust mite extract-*Dermatophagoides farinae* (Der f). Der f sensitization induces AHR that is prevented by acute (2) nebulization (FIG. 4B), suggesting that (2) inhibits in vivo Rac to induce bronchodilation.

In conclusion, the lead molecule (2) is a new selective and potent Rac inhibitor that could open up a new avenue for the treatment of pulmonary pathologies characterized by AHR.

The invention claimed is:

1. A method for treating a pathology characterized by bronchoconstriction, comprising administering to a mammal in need thereof a therapeutically effective amount of a compound having the following formula (VI):

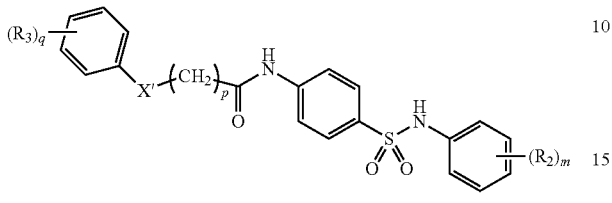

(VI)

wherein:
- p is an integer from 1 to 3 inclusive,
- X' is chosen from the group consisting of: —S—, —NH—, —NR$_d$—, —CH$_2$—, —SO$_2$—, and —SO—, R$_d$ being H or a (C$_1$-C$_6$)alkyl group;
- q is 0 or is an integer from 1 to 5 inclusive,
- the R$_3$ groups, identical or different, are chosen from the group consisting of: (C$_1$-C$_6$)alkyl groups, halogen atoms, (C$_1$-C$_6$)alxoxy groups, (C$_1$-C$_6$)thioalkyl groups, and —NR$_a$R$_b$ groups, R$_a$ and R$_b$, identical or different, being H or a (C$_1$-C$_6$)alkyl group;
- m is 0 or is an integer from 1 to 5 inclusive,
- the R$_2$ groups, identical or different, are chosen from the group consisting of: halogen atoms, (C$_1$-C$_6$)alkyl groups, (C$_1$-C$_6$)alkoxy groups, (C$_1$-C$_6$)thioalkyl groups, —SCF$_3$, —SF$_5$, and —NR$_a$R$_b$ groups, R$_a$ and R$_b$, identical or different, being H or a (C$_1$-C$_6$)alkyl group.

2. The method of claim 1, wherein the pathology characterized by bronchoconstriction is asthma.

3. The method of claim 1, wherein the compound has the following formula (VII):

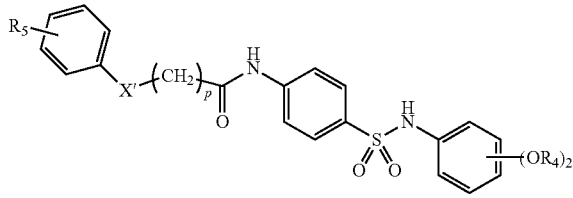

(VII)

wherein:
- R$_5$ is a (C$_1$-C$_6$)alkyl group; and
- the R$_4$ groups, identical or different, are chosen from the (C$_1$-C$_6$)alkyl groups.

4. The method of claim 1, wherein the compound has the formula (VI) wherein X' is —S— or —CH$_2$—.

5. The method of claim 1, wherein the compound has the formula (VI) wherein X' is —S—.

6. The method of claim 1, wherein the compound has the formula (VI) wherein q is 0 or 1, and the R$_3$ groups, identical or different, are chosen from the group consisting of: (C$_1$-C$_6$)alkyl groups, and (C$_1$-C$_6$)alxoxy groups.

* * * * *